(12) United States Patent
Groger et al.

(10) Patent No.: US 6,521,185 B1
(45) Date of Patent: Feb. 18, 2003

(54) FLUORESCENT PROBES BASED ON THE AFFINITY OF A POLYMER MATRIX FOR AN ANALYTE OF INTEREST

(75) Inventors: Howard P. Groger, Gainesville, FL (US); Shufang Luo, Blacksburg, VA (US); K. Peter Lo, Blacksburg, VA (US); Martin Weiss, New Port Richey, FL (US); James M. Sloan, Abingdon, MD (US); Russell J. Churchill, Radford, VA (US)

(73) Assignee: American Research Corporation of Virginia, Radford, VA (US)

( * ) Notice: Subject to any disclaimer, the term of this patent is extended or adjusted under 35 U.S.C. 154(b) by 1159 days.

(21) Appl. No.: 08/553,773

(22) Filed: Oct. 23, 1995

(51) Int. Cl.[7] .............................................. G01N 21/64
(52) U.S. Cl. ................................ 422/82.08; 422/82.07; 436/172
(58) Field of Search ........................... 422/82.05, 82.06, 422/82.07, 82.08, 82.11, 91; 436/104, 172

(56) References Cited

U.S. PATENT DOCUMENTS

| | | | |
|---|---|---|---|
| 5,573,956 A | * 11/1996 | Hanning | 436/164 |
| 5,621,522 A | * 4/1997 | Ewing et al. | 356/301 |
| 5,641,640 A | * 6/1997 | Hanning | 436/164 |
| 5,674,752 A | * 10/1997 | Buckley et al. | 436/151 |

OTHER PUBLICATIONS

DuPont Product Information Sheet for Nafion® (Sep. 2001).*
Safety Data Sheet for nile blue 690 perchlorate (Mar. 3, 1999).*
Material Safety Data Sheet for Oxazine 750 Perchlorate, Exciton, Inc. (no date).*

(List continued on next page.)

Primary Examiner—Jill Warden
(74) Attorney, Agent, or Firm—James Creighton Wray; Meera P. Narasimhan

(57) ABSTRACT

A highly-sensitive, rapid response fluorescent probe is based on the affinity of a polymer matrix for an analyte of interest. The probe includes a polymer matrix and a dye immobilized in the matrix. The polymer matrix has an affinity for an analyte of interest and the dye has little or no sensitivity to the analyte of interest when excited by an excitation source in a free state but has significant sensitivity to the analyte of interest when excited by the excitation source when immobilized in the matrix. Sensors incorporating the polymer/fluorophore probes of the present invention have the sensitivity and rapid response needed for detection of chemical agent and biological materials. Sensors using the probes provide sensitivity to Sarin at several hundred parts per trillion in one second or less. That is a notable advance over state-of-the-art detectors that require preconcentration steps, which in turn restrict response times to one minute or more. A wide-range of near-infrared excitable fluorophores are used as sensitive probes for analytes not detectable when the fluorophores are outside the polymer matrix. The present sensors provide early warning of the presence of toxic chemicals, provides for on-line analysis of trace materials in chemical and biological processing operations and biomedical processing operations, and provides for effective biomedical and environmental monitoring.

10 Claims, 14 Drawing Sheets

OTHER PUBLICATIONS

STN Search of CAS Registry for Reg. Nos. 62669–60–7 and 54849–69–3 (Oct. 1,2002).*

Giuliani, J. F., "An Investigation of the Solubility of Organic Vapors in Polymer Films Using an Optical Wave Guide Interfacial Probe," Journal of Polymer Science, 1988, pp. 2197–2201, vol. 26.

Giuliani, J. F., "The Effect of Ammonia Ions on the Absorption and Fluorescence of an Oxazine Dry, "Spectroscopy Letters, vol. 16, No. 7 pp. 555–563, 1983.

Giuliani, J. F., "Selective Response of Polymeric–Film– Coated Optical Waveguide Devices to Water and Toxic Volatile Compounds," Fundamentals and Applications of Chemical Sensors, ACs Symposium Series, vol. 309, pp. 320–329, 1986.

Giuliani, J. F., "Reversible Optical Waveguide Sensor for Ammonia Vapors," Optics Letters, vol. 8, No. 1, pp. 54–56, 1983.

* cited by examiner

FIG. 24

| Dye | Excitation Wavelength (nm) | Emission Wavelength (nm) | Percent Quenching |
|---|---|---|---|
| Nile Blue 690 | 523 | 583 | 15.5 |
| Quinaldine Red | 531 | 612 | --- |
| Phenosafranin | 542 | 567 | 4.3 |
| Rhodanile Blue | 627 | 667 | 10.9 |
| Brilliant Cresyl Blue | 634 | 663 | --- |
| Oxazine 170 | 638 | 655 | 41.2 |
| HIDC Iodide | 647 | 675 | 15.5 |
| IR 144 | 710 | 796 | 21.4 |
| DTTC Iodide | 762 | 791 | 33.9 |

FIG. 25

| Dye | Excitation Wavelength (nm) | Emission Wavelength (nm) | Percent Quenching |
|---|---|---|---|
| Nile Blue 690 | 645 | 670 | 0.9 |
| Quinaldine Red | 529 | 606 | 8.1 |
| Phenosafranin | 522 | 564 | 8.1 |
| Rhodanile Blue | 560 | 586 | 0.05 |
| Brilliant Cresyl Blue | 624 | 659 | 4.0 |
| Oxazine 170 | 626 | 660 | 1.1 |
| HIDC Iodide | 646 | 671 | 2.6 |
| IR 144 | 548 | 582 | 12.4 |
| Methylene Blue | 764 | 823 | 45.9 |
| DTTC Iodide | 670 | 764 | 16.6 |

FLUORESCENT PROBES BASED ON THE AFFINITY OF A POLYMER MATRIX FOR AN ANALYTE OF INTEREST

This project was funded by the Department of the Army, Small Business Innovation Research Program of the U.S. Army Laboratory Command under Contract Number DAAL01-93-C-4049.

BACKGROUND OF THE INVENTION

This invention relates to apparatus for and methods of rapidly and sensitively detecting and monitoring chemical and biological materials.

Recent developments in the world political situation, exemplified by the demise of the Soviet Union, continued geopolitical pressures in the Middle East and Eastern Europe and the proliferation of terrorist activities throughout the world, have raised increased concerns about the use of chemical and biological warfare materials in local conflicts. The defense against chemical and biological warfare agents includes detection of potential threats, development and use of protective equipment, development of vaccination post-exposure prophylaxis measures and fabrication of structures providing barriers to the toxic agents which are suitable for decontamination procedures. Threat identification is imperative prior to engagement, during battle and after battle during decontamination procedures. In addition, chemical sensors for detecting chemical warfare materials are needed for treaty verification, demilitarization, environmental monitoring and characterization of materials acting as barriers to agent diffusion.

Existing methods of detection have proven inadequate. Existing methods for long-range threat identification, such as light detection and ranging (LIDAR), and for laboratory analysis of chemical warfare agents using gas chromatography to provide a chemical agent monitor (miniCAMS), light addressable potentiometric sensor (LAPS) or ion mobility sensor (IMS) technology, have proven slow and cumbersome to carry out. Needs exist for lightweight, high-sensitivity sensors having rapid response times.

Existing sensors have proven capable of meeting the requirements of several applications but no sensor has provided the combined sensitivity and speed of response needed for each application. Needs exist for field-usable chemical and biological sensors for the detection of vapor and liquid dispersed chemical warfare agents, toxins of biological origin and aerosol dispersed pathogenic microorganisms. Existing instrumentation used in identifying chemical warfare agents rely on ion mobility spectroscopy or gas chromatography for detection. The Advanced Chemical Agent Detection/Alarm System (ACADA) uses ion-mobility spectroscopy to achieve sensitivities to Sarin and Soman on the order of 1 mg/m$^3$ (170 parts per billion (ppb)) in ten seconds and 0.1 mg/m$^3$ (17 ppb) in 30 seconds. In addition to the system's slow response and low sensitivity, the size and weight characteristics of the ACADA system (one cubic foot in volume and 25 pounds in weight) reduce the applicability of the system for distributed sensing or remote sensing applications. Sensors such as the miniCAMS system provide unparalleled sensitivity but require preconcentration times on the order of minutes. That response time is unsuitable for rapid detection of conditions that are immediately dangerous to life and health. Other existing methods use acoustic or optical/electrochemical methods of detection, such as surface acoustic wave (SAW)-based instruments and light addressable potentiometric sensors (LAPS). Neither method has proven effective in meeting the sensitivity and response times required. At best, the SAW instrument has demonstrated sensitivities to Sarin/Soman at 0.01 mg/m$^3$ (1.7 ppb), but requires preconcentration times ranging from 2 minutes to 14 minutes. Needs exist for field-usable sensors that provide for highly-sensitive, rapid response measurements of the concentration of analytes in solution or in air.

Previous efforts indicate that polymers can be used to improve the sensitivity of SAW devices to a range of analytes and that polymer coatings are effective in enhancing the concentrations of analyte detected by optical probes. Polymer-coated waveguides have been used to detect nerve agent simulants, such as dimethyl-methyl-phosphonate (DMMP), and polymeric materials having affinity for the nerve agent and exhibiting a change in refractive index upon absorption of the agent have been identified. Floropolyol was found to have a partition coefficient for vapor phase DMMP between one million and ten million, indicating that the concentration of DMMP in the fluoropolyol was up to ten million times that in the vapor phase. Fluoropolyol is strongly acidic, which may improve sensitivity to strongly basic vapors such as the organophosphorus compounds. No sensors have been developed, however, that have short response times and high sensitivity, that are low cost and that are easily and safely incorporated into small, portable packages for deployment in rugged domains. Needs exist for optical chemical and biological sensors having those characteristics for use in a network of point detectors for multiple applications, including monitoring decontamination of military field structures, detecting chemical and biological agents in chemical treaty verification, assisting in reconnaissance of battlefield and depot perimeters, demilitarization exercises and monitoring breakthrough times associated with polymeric or other complex structural materials.

The far-visible and near-infrared (IR) spectral regions (600–1000 nm) are areas of low interference, where only several classes of molecules exhibit significant absorption and fluorescence. The use of near-IR labels in sensor design is becoming increasingly important due to the advent of semiconductor-based light sources and detectors and the reduced interference in the near-IR wavelength range. Heptamethine cyanine dyes have been shown effective in labeling nucleic acid materials. For biomolecule labeling and for analytes containing primary amino functional groups, isothiocynate derivatives of those cyanine dyes are the most suitable labels because they form stable thioureas. Needs exist for sensors for use in biochemical applications that use near-IR fluorophores.

Needs exist for low-cost sensors exhibiting rapid response at very low concentrations of chemical warfare agent and simulant materials. Needs also exist for laser-based sensors that can be used commercially in biomedical, industrial and environmental applications requiring on-site, rapid and sensitive chemical and biological analysis. In the field of biomedical testing, there is great need for point-of-care monitoring of physiological conditions and disease producing microorganisms. In the food industry, there is a need for sensors for product quality control and distributed process control applications. Needs for rapid, sensitive, small, portable and inexpensive sensors are also needed in the chemical and pharmaceutical processing industries, and in the area of pollution monitoring. Needs exist for sensors that can meet the sensitivity and time response requirements dictated by each industry and that are of a reasonable size and cost.

SUMMARY OF THE INVENTION

A highly-sensitive, rapid response fluorescent probe is based on the affinity of a polymer matrix for an analyte of interest.

The polymer/fluorophore probes of the present invention have the sensitivity and rapid response needed for detection of chemical agent and biological materials. Sensors using the probes provide sensitivity to Sarin at several hundred parts per trillion without the need for preconcentration steps. The lack of necessity for preconcentration allows vapors to be detected in one second or less. That is a notable advance over state-of-the-art detectors that require preconcentration steps, which in turn restrict response times to one minute or more.

Fluorescent dyes showing little or no sensitivity to an analyte of interest provide significant sensitivity to that same analyte of interest as long as a polymer having affinity for the analyte is employed as the matrix. A wide-range of near-infrared excitable fluorophores are used as sensitive probes for analytes not detectable when the fluorophores are outside the polymer matrix. The present sensors provide early warning of the presence of toxic chemicals, provide for on-line analysis of trace materials in chemical and biological processing operations and biomedical processing operations, and provide for effective biomedical and environmental monitoring.

Organic thin films having affinity for particular analytes and the immobilization of fluorescent dyes in those films to produce a sensitive apparatus and method for detecting chemical and biological materials. Perfluorinated, ionophoric polymeric materials produce self-assembled structures which, in the presence of semiconductor diode laser-excitable dyes, respond to targeted chemical or biological agents. The combination of thin polymer films with near-IR excitable dyes has advantages that include:

the diffusion and reaction zones of a sensor based on a fluorophore immobilized in a polymer matrix has reduced dimensions, thereby resulting in rapid sensor response;

organized thin polymer films are compatible with silicon, gallium arsenide, indium phosphide and silicon carbide semiconductor materials, thereby allowing optical integration into a small, rugged sensor package;

near-IR fluorophores are excited in a wavelength region where there are fewer interferences than observed with excitation in ultraviolet or visible regions of the spectrum and the compatibility of near-IR fluorophores with semiconductor diode laser excitation further contributes to improved signal-to-noise ratio with minimal package size;

since semiconductor diode lasers are inexpensive, rugged and suitable for field use, sensors developed based on fluorophores excitable by semiconductor diode lasers can be manufactured inexpensively and packaged for portability or for use in an array of point detectors.

In the present invention, thin films, such as poly(ethylene-maleic anhydride) (PEM), poly(vinyl pyridine) (PVP) and Nafion® films, are deposited on glass substrates and on polymer optical waveguides. The films are deposited with fluorescent materials sensitive to chemical agents and simulants. Preferably, the fluorescent material is selected from a wide range of near-IR fluorophores. The fluorophores in the thin polymer film are responsive to dimethyl methylphosphonate or nerve agent. Numerous polymer/fluorophore combinations are possible, each being capable of ameliorating present limitations in response times at low agent concentrations.

Several polymers are possible for use as the immobilization matrix for fluorescent dyes. When near-IR fluorescent dyes are incorporated in the matrix, sufficiently rapid response to nerve agent stimulants is provided to allow for real time detection of those materials. In one embodiment, Nafion® thin films with hexamethylindodicarbocyanine membrane potential-sensitive dyes are used in conjunction with semiconductor diode lasers to detect Sarin at concentrations as low as 500 parts per trillion (ppt). The sensor response time is approximately one second. The sensor is reversible to Sarin, in that removal of the chemical agent results in return of the original fluorescence level in about one second. The rapid response to Sarin represents an advance in the state-of-the-art of detection.

Chemical sensors using the thin polymer film/fluorescent material combination of the present invention provides for increased selectivity in the detection of chemical warfare and toxins of biological origin. The use of a semiconductor diode laser in the present sensor provides sensitivities compatible with single mode excitation and detection through interaction of the evanescent field of an optical waveguide with a chemically sensitive film deposited on the waveguide surface.

Sensors developed based on the polymer/fluorophore probes meet the requirements mandated for military applications. The present sensors detect nerve agent GB (Sarin) at concentrations less than 500 parts per trillion with a response and cleardown time of less than one second. No existing instruments provide response to that level in as short a time. The enhanced sensitivity of a membrane potential dye immobilized in a ionomeric, amphiphilic polymer film results from the unique charge environment in the vicinity of the dye. The most sensitive polymer/fluorophore probes respond irreversibly to a number of interferents but reversibly to chemical agents and simulants. Less sensitive polymer/fluorophore probes respond reversibly to both simulant and interferences.

The immobilization of fluorophores in polymeric matrices with enhanced affinity for an analyte of interest provides improved sensitivities over sensors fabricated with the same fluorophores in polymers with little or no affinity to the analyte of interest. That demonstrates the compatibility of surface acoustic wave sensor data with the selection of polymers suitable for optical detection. In particular, amphiphilic polymers combined with membrane potential sensitive dyes are particularly valuable for the detection of hazardous vapors. Similarly, polymer materials such as poly(ethylene-maleic anhydride) (PEM), poly(vinyl pyridine) (PVP) or Nafion®, having a known affinity for dimethyl methylphosphonate (DMMP), when used in conjunction with fluorescent dyes, function as probes that are sensitive to DMMP. In one embodiment, reversible probes are produced using solvatochromic fluorophores immobilized in polymers having an affinity for an analyte of interest. Probes fabricated from PVP or PEM also respond reversibly to DMMP as well as to interferents such as ammonia.

The enhanced sensitivity of a membrane potential dye immobilized in an ionomeric, amphiphilic polymer, such as Nafion® film, to an analyte of interest, such as the nerve agent Sarin, results from the unique charge environment in the vicinity of the dye. Similar sensitivities are achieved using other matrices, including poly(ethylene-maleic anhydride) (PEM) or poly(vinyl pyridine) (PVP) on glass slides after doping with nile red or nile blue.

Diode laser excitation has advantages over excitation using conventional light sources. Instrument size is reduced by using diode lasers rather than conventional light sources. Semiconductor diode lasers are also noted for long operational lifetimes, in the range of $10^5$ h.

Using a small sensor having the polymer/fluorescent probe, nerve gas is detected at 500 parts per trillion.

Benzene, xylene and toluene are detectable at trace concentrations by using one of a wide range of semiconductor laser excitable dyes. Ammonia is also detectable at trace concentrations using the present invention. By employing differing dyes immobilized in differing polymer matrices, nearly any chemical can be identified and detected.

In addition to military applications, sensors having the polymer/fluorophore probes have potential biomedical, environmental, commercial and industrial applications. The present sensor can be used in environmental chemical and biological detection, including the monitoring of waste sites and ground water quality control, and in process evaluation and hazard analysis for quality control in the food processing, biotechnological and materials processing industries. The reduced cost and portability of the sensor offers advantages in process inspection, in point-of-care medical diagnosis and in environmental site monitoring.

A fluorescent probe apparatus for use in a sensor includes a polymer matrix and a dye immobilized in the matrix. The polymer matrix has an affinity for an analyte of interest and the dye has little or no sensitivity to the analyte of interest when excited by an excitation source in a free state but has significant sensitivity to the analyte of interest when excited by the excitation source when immobilized in the matrix. The dye is preferably a fluorescent dye that includes near-infrared fluorophores. The polymer matrix is preferably a poly(ethylene-maleic anhydride) matrix, a poly(vinyl pyridine) matrix, a poly(4-vinyl-phenol) bromonated matrix, or a Nafion® matrix.

In preferred applications, the analyte of interest is selected from the group consisting of dimethyl methylphosphonate, Sarin, benzene, xylene, toluene and ammonia.

In a preferred embodiment of the probe, the dye is a membrane potential sensitive dye and the polymer matrix is a micelle forming polymer matrix or a reverse micelle forming polymer matrix. In one embodiment, the membrane potential sensitive dye is 1,1'3,3,3',3'-hexamethylindotricarbocyanine iodide and the matrix is a Nafion® matrix.

In another embodiment, the dye is a fluorophore dye, the polymer matrix is a poly(isoprene/fluoro alcohol) matrix or a poly (ethyleneimine) matrix, and the analyte of interest is a hydrogen-bond forming material.

In another embodiment, the dye is nile red or nile blue, and the polymer matrix is a poly(ethylene-maleic anhydride) matrix or a poly(vinyl pyridine) matrix.

In a preferred embodiment of the probe, the dye is selected from the group consisting of nile blue 690 (5-amino-9-(diethylamino)-benzo[a]phenoxazin-7-ium perchlorate, quinaldine red, phenosafranin, rhodanile blue, Oxazine 750 (2,3,6,7-tetrahydro-5-(ethylimino)-1H,5H-benzo[a]phenoxazin-[8,9,10-ij]quinolizin perchlorate, Oxazine 170 (CAS Reg. 62669-60-7), (5,9-bis(ethylamino)-10-methyl-benzo[a]phenoxazin-7-ium perchlorate, brilliant crescyl blue, 3,3'-diethylthiatricarbocyanine iodide, 1,1'3,3, 3',3'-hexamethylindodicarbocyanine iodide, IR-144 (CAS Reg. 54849-69-3) and methylene blue, and the polymer matrix is selected from the group consisting of a Nafion® matrix, a poly(ethylene maleate) matrix and a poly(vinyl pyridine) matrix.

The analyte of interest can be a live chemical agent. When a live agent is the analyte of interest, the dye is preferably nile blue perchlorate, 1,1'3,3,3',3'-hexamethylindodicarbocyanine iodide or Oxazine 750.

A method for chemical sensing includes the steps of immobilizing a dye in a polymer matrix to form a polymer/dye probe, depositing the probe on a substrate, exciting the probe positioned on the substrate, exposing the probe on the substrate to an analyte of interest, and detecting a change in the sensitivity of the dye immobilized in the polymer matrix of the probe. The method can further include the step of adding a strong base to the polymer matrix prior to or concurrently with the immobilizing step. Preferably, the strong base is sodium hydroxide or ammonium hydroxide.

In preferred embodiments, the depositing step is performed by spin coating or solution casting.

The present method can further include baking the probe/substrate combination after the depositing step. The baking step is preferably carried out in a nitrogen atmosphere.

The probe may be deposited on a glass slide substrate.

A highly-sensitive, rapid response sensor apparatus for detecting chemical and biological agents includes a dye/polymer probe, a waveguide connected to the probe, an excitation source for providing light to the waveguide and for exciting the dye, and a detector for detecting a response from the probe. The probe further includes a polymer matrix and a dye immobilized in the matrix. The polymer matrix has an affinity for an analyte of interest and the dye has little or no sensitivity to the analyte of interest when excited by the excitation source in a free state but has significant sensitivity to the analyte of interest when excited by the excitation source when immobilized in the matrix. The excitation source is preferably a semiconductor diode laser and the detector is a photomultiplier tube or an amplified photodiode.

In a preferred embodiment, the probe of the sensor includes a series of dye/polymer matrix probes that respond reversibly to the analyte of interest and to interferents.

In a preferred embodiment, the sensor further includes a modulator connected to the excitation source and to the detector for direct modulation of the excitation source. The modulator preferably includes a gain-phase analyzer connected to the detector and a bias tee connected to the analyzer and to the excitation source.

These and further and other objects and features of the invention are apparent in the disclosure, which includes the above and ongoing written specification, with the claims and the drawings.

BRIEF DESCRIPTION OF THE DRAWINGS

FIG. 24 is a table showing the quenching of fluorophore dyes in poly(vinyl pyridine) in the presence of dimethyl methylphosphonate.

FIG. 25 is another table showing the quenching of fluorophore dyes in poly(vinyl pyridine) in the presence of dimethyl methylphosphonate.

DETAILED DESCRIPTION OF THE PREFERRED EMBODIMENTS

Figure 1:
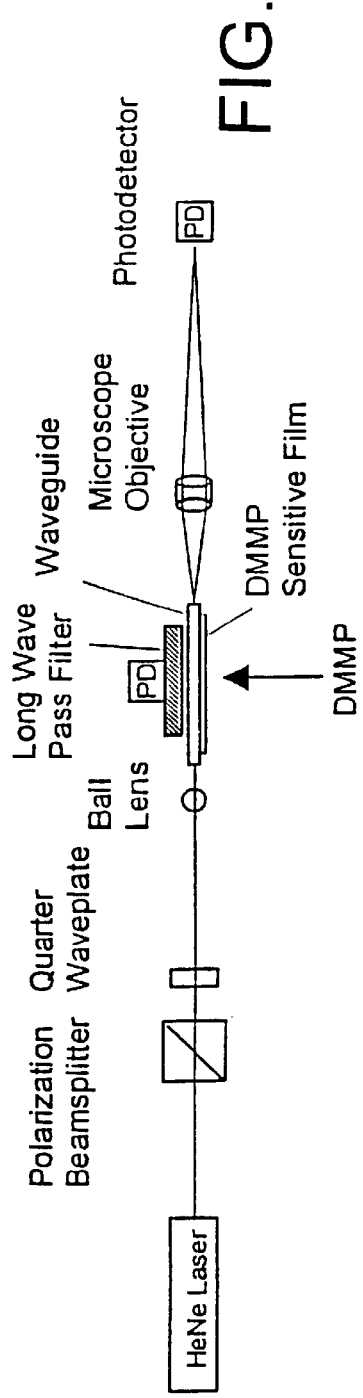
FIG. 1 is a setup for detection of DMMP using Oxazine 170/Nafion® on waveguide.

Referring to the drawings, a fluorescent probe apparatus for use in a sensor includes a polymer matrix and a dye immobilized in the matrix. The polymer matrix has an affinity for an analyte of interest and the dye has little or no sensitivity to the analyte of interest when excited by an excitation source in a free state but has significant sensitivity to the analyte of interest when excited by the excitation source when immobilized in the matrix. The dye is preferably a fluorescent dye that includes near-infrared fluorophores. A highly-sensitive, rapid response sensor apparatus for detecting chemical and biological agents that includes the dye/polymer probe is also disclosed. The sensor includes the dye/polymer probe, a waveguide connected to the probe, an excitation source for providing light to the waveguide and for exciting the dye, and a detector for detecting a response from the probe. The excitation source is preferably a semiconductor diode laser and the detector is a photomultiplier tube or an amplified photodiode. Optics, such as a polarization beamsplitter, a quarter wave plate and a ball lens, or a combination of those optics, can be positioned between the excitation light source and the waveguide for focusing the light beam. A filter can be incorporated with the detector.

The examples provided in the following disclosure are only exemplary and in no way limit the scope of applicant's invention.

Efforts were directed toward screening matrix-fluorophore combinations leading to a sensitive receptor structure for the detection of chemical agents, such as warfare agents and simulants. Polymer matrices were used to entrap the fluorophores.

Work was performed to screen polymer-fluorophore combinations for sensitivity to dimethyl methyl phosphonate (DMMP). Screening involved the acquisition of absorption and fluorescence spectra from thin films of poly(ethylene-maleic anhydride) (PEM), polyvinyl pyridine (PVP) and Nafion® on glass slides after doping with nile red or nile blue. PEM films were prepared by adding 0.2 g of polymer to 20 ml of acetone. PVP was prepared by dissolving 0.1 g of polymer in 20 ml of chloroform. Fluorescent polymer/dye probes were prepared to 3.9×10$^{-4}$M of nile red or 1.56×10$^{-3}$M of nile blue in polymer and solvent. Glass slides were dip-coated in solutions containing polymer and dye to a thickness in the range 0.06 to 1.0 mm. Samples of nile red/PEM or PVP were excited using either the 488 nm or 514 nm line of a 1 mW argon-ion laser. Samples of nile blue/PEM were excited using a 3 mW helium-neon laser emitting at 632.8 nm. Interaction with vapor DMMP was accomplished either by placing the sample in the vicinity of the liquid at room temperature or by heating the liquid to increase the vapor pressure.

Work was performed to extend initial screening efforts for incorporating nile blue 690, quinaldine red, phenosafranin, rhodanile blue, Oxazine 170, brilliant crescyl blue, 3,3'-diethylthiatricarbocyanine iodide (DTTC) iodide), 1,1'3,3,3'3'-hexamethylindodicarbocyanine iodide (HIDC iodide), IR-144 (Kodak Laboratory Chemicals) and Methylene Blue in poly(ethylene maleate) or poly(vinyl pyridine). Dye solutions were prepared to 10$^{-4}$ using either methanol or acetone as solvent. Poly vinyl pyridine) coatings were prepared using either methanol or acetone as solvent. Poly (vinyl pyridine) coatings were prepared using 3 ml of the dye solution containing methanol solvent and 0.07 g of polymer. Poly (ethylene maleate) coatings were prepared using 3 ml dye solution containing acetone solvent and 0.1 gram polymer. The excitation and emission spectra were obtained using a SPEX fluorimeter with a xenon lamp source. DMMP vapor was generated by placing approximately 0.0158 g, or 0.0122 ml of liquid DMMP in a heating mantle inside the sample cell and applying current to the heating mantle, resulting in complete vaporization of the drop in 3 to 5 minutes. It is estimated that the polymer/dye probe is exposed to approximately 54 micrograms of material in a 392 cubic centimeter volume. Fluorescence quenching of the polymer/dye probe was measured by comparison of the probe emission in the presence of the vapor to the emission of the probe in the absence of the DMMP vapor.

Experiments were performed to determine the sensitivity of dyes immobilized in Nafion® to DMMP. DTTC iodide (3,3'-diethylthiatricarbocyanine iodide), IR 144 and Rhodamine 700 were immobilized in Nafion® ion-exchange material (Aldrich 27,470-4). Dye solutions were prepared to 10$^{-4}$M using methanol as the solvent. The dye/Nafion® coating was prepared by pipetting one ml of solution onto a glass slide and allowing the methanol solvent to evaporate. The samples were exposed to DMMP through either using the mantle heater to evaporate the DMMP or through heating the DMMP below the sample surface. Work was performed for screening Nafion®-fluorophore combinations for sensitivity to DMMP. Nile red, nile blue A, Oxazine 170 and Oxazine 750 were incorporated in Nafion® and exposed to DMMP vapor at varying concentrations. Work was performed to determine the lower limits of detection of a membrane potential-sensitive dye in a Nafion® matrix in the presence of DMMP vapor. Experiments were performed using $10^{-4}$M solution of 1,1',3,3',3'-hexamethylindodicarbocyanine iodide (DiIC$_1$(5)) dissolved in 0.5 weight % Nafion®-ethanol solution drop-coated on a soda lime glass slide.

Work has also been performed to investigate the use if dyes immobilized in pre-imidized photosensitive polyimide waveguides for the detection of chemical warfare materials. Polyimide materials have proven effective in providing insulation in semiconductor diode laser structures. Probimide 414 (OCG Microelectronic Materials, Inc.) was spin-coated along with adhesion promoter onto cleaned glass slides to form waveguides from 5 to 10 mm thick. The waveguide structure was baked at approximately 230° C. in nitrogen. The waveguides were placed in dye solutions containing Oxazine 720 or nile blue A dyes. After dye diffusion, the polyimide/dye probe was then exposed to ultraviolet light at 365 nm wavelength and approximately 0.75 Joule per square centimeter intensity.

A chemically sensitive waveguide sensor structure was also fabricated using a clear polyimide waveguide structure with a dye/polymer thin film deposited over the top of the waveguide. Clear polyimide waveguide structures were prepared by the above method omitting the dye-diffusion step. Chemically sensitive thin films were prepared by drop-casting of the fluorescence dye doped polymer onto the waveguides. A $10^{-4}$M solution of Oxazine 170 was dissolved in 0.5 weight % Nafion®-ethanol solution and drop-coated on the polyimide optical waveguide. The fluorophore/polymer waveguide was exposed to DMMP vapor by adding several drops of liquid of DMMP to a glass slide and positioning the waveguide face-downward over the glass slide at room temperature. Work was performed to add a polarization beamsplitter and a quarter-wave plate between the laser source and the waveguide to reduce optical feedback and improve sensor stability. A schematic diagram of the sensor arrangement is shown in FIG. 1.

Examples are provided for showing the use of polymeric immobilization in enhancing the sensitivity of a fluorescent chemical sensor. Work was performed to determine the lower limits of detection of a membrane potential-sensitive dye, 1,1',3,3,3',3'-hexamethylindodicarbocyanine iodide (DiIC$_1$(5)), in a Nafion® matrix in the presence of vapor dimethyl methyl phosphonate (DMMP). It may be noted that DiIC$_1$(5) displays little or no sensitivity to DMMP when apart from the Nafion® matrix. Nafion® is formed when tetrafluorethylene is copolymerized with a perfluorovinyl ether containing sulfonate or carboxylate functional end groups. The fluorocarbon phase of the polymer is incompatible with the aqueous ionic phase leading to considerable phase separation. Prior work has shown that a sulfonate-based Nafion® exhibits a dense texture of dark areas ca. 5 nm in diameter which are homogeneously distributed in the film when observed with bright-field transmission electron microscopy. The formation of sulfonate ionic clusters provides hydrophilic regions surrounded by nonpolar hydrophobic chain material. Electron infraction measurements indicate that the fluorocarbon backbone of Nafion® is in the form of a linear zigzag chain with a reproducible orientation with the c-axis perpendicular to the plane of the film. It is thought that the side chains of the Nafion® prevent twisting of the fluorocarbon backbone and stabilize the configuration of the film. Part of the activity of the Nafion® film is thought to arise from the transport properties of the film. The properties of cationic dyes such as methylene flue, thionine, safranine and meldola blue in Nafion® and found diffusion coefficients as high as $9 \times 10^{-7}$ cm$^2$ s$^{-1}$ at low dye concentrations ($3.5 \times 10^{-4}$M) within the film show a dramatic decrease with increasing concentration. It was suggested that the diffusion of cationic dyes in Nafion® decreased with increasing dye concentration as a result of the formation of aggregates within the polymer. The use of a membrane potential sensitive dye immobilized in Nafion® thin films presents a particularly sensitive approach to chemical sensing. The Nafion® thin films contain negatively charged sites as a result of the sulfonate or carboxylate functional groups present within the polymer. More positive sites can be formed by ion-exchange processing of the film or through selection of a suitable starting material. The immobilized membrane-potential sensitive dyes can respond to changes in the localized dipole potential formed by the orientation of charged groups in the vicinity of hydrophilic regions of the polymer surrounded by nonpolar hydrophobic chain material or to changes in the aggregation of the dye produced by changes in the molecular distances between segments of the zig-zag polymer chain.

Figure 2:
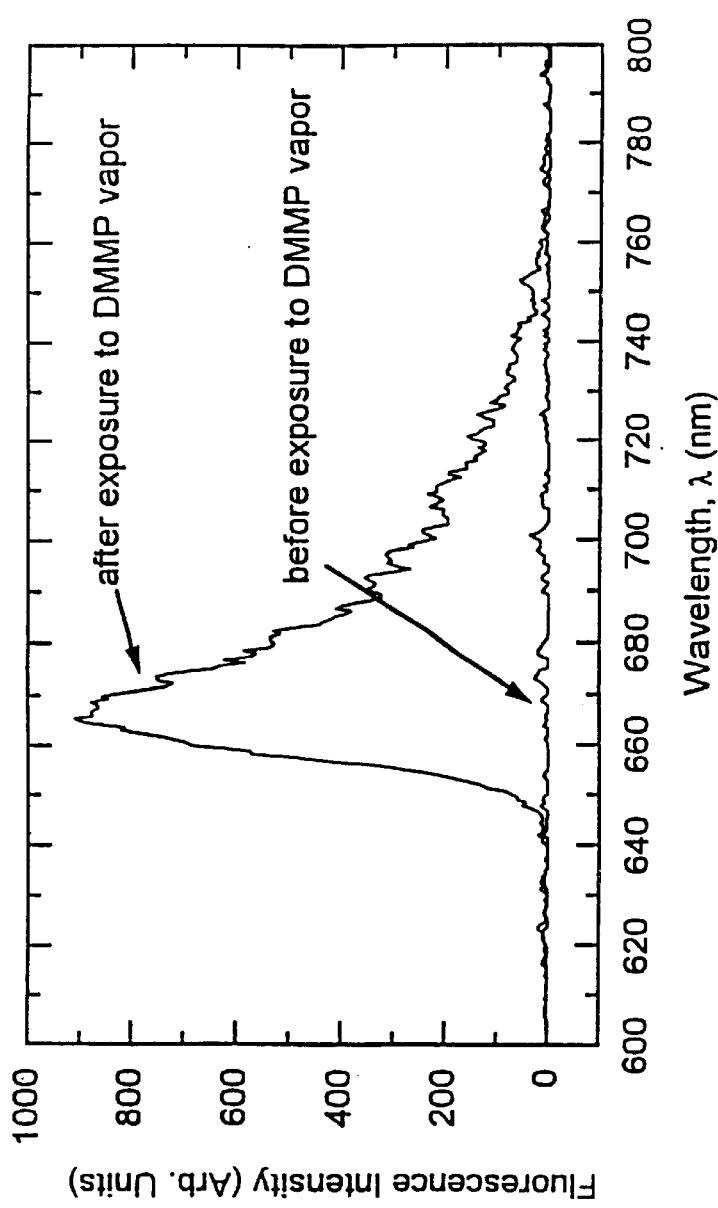
FIG. 2 is an emission spectra of air-dried Nafion® thin film containing DiIC$_1$(5) before and after exposure to DMMP vapor.

Experiments were performed using a $10^{-4}$M solution of DiIC$_1$(5) dissolved in 0.5 weight % Nafion®-ethanol solution drop-coated on a soda lime glass slide. Air-dried samples showed almost no fluorescence in the absence of DMMP when excited with a helium-neon laser. In the presence of 440 ppm DMMP the fluorescence was found as shown in FIG. 2 (Figure from Phase II report). Evaluation of the ultraviolet-visible (UV-Vis) spectrum of the air-dried sample shows a broad absorption spectrum which is considerably narrowed and increased in intensity after exposure to DMMP. It was determined that films of DiIC$_1$(5) in Nafion® could be used in an absorption mode to detect concentrations of DMMP as low as 20 ppm.

Figure 3:
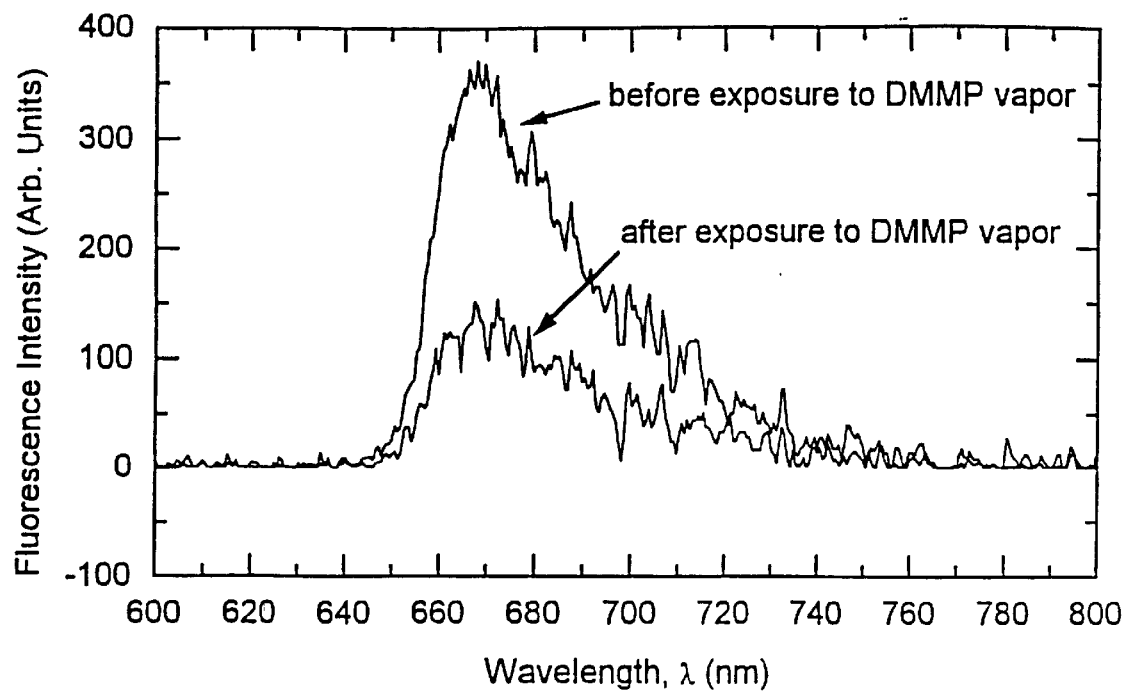
FIG. 3 is an emission spectra of oven-dried Nafion® thin film containing DiIC$_1$(5) before and after exposure to DMMP vapor.
Figure 4:
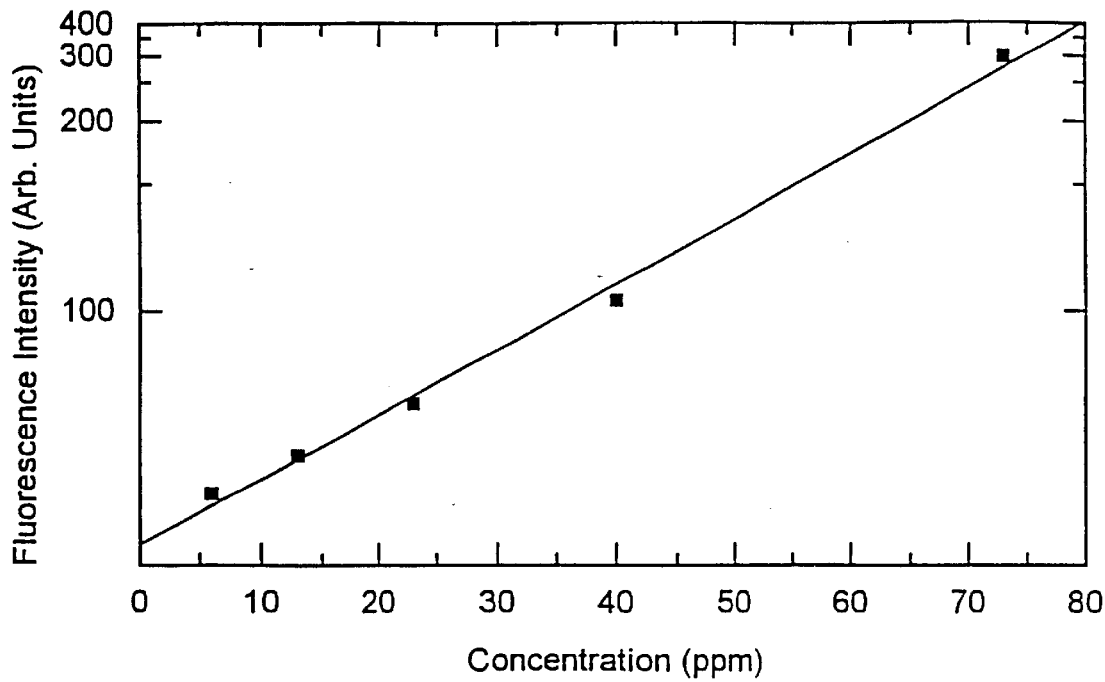
FIG. 4 shows a change in fluorescence of DiIC$_1$ (5)/Nafion® film upon exposure to DMMP vapor at concentrations from 6 to 73 ppm.
Figure 5:
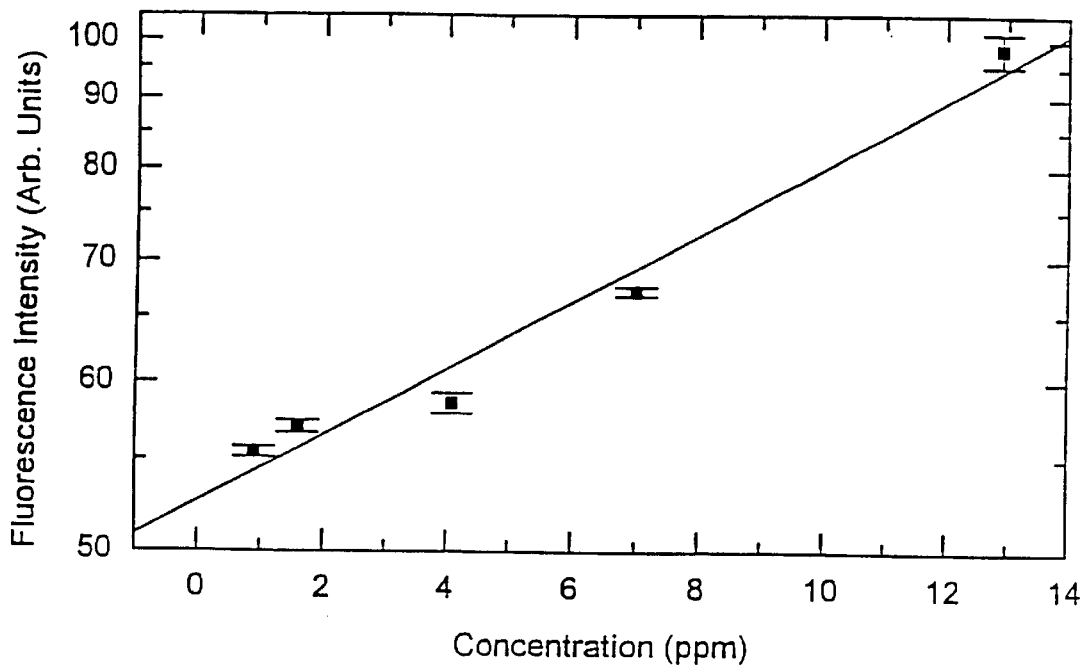
FIG. 5 shows a change in fluorescence of DiIC$_1$(5)/Naifon® film upon exposure to DMMP vapor at concentrations from 0.9 to 13 ppm.
Figure 6:
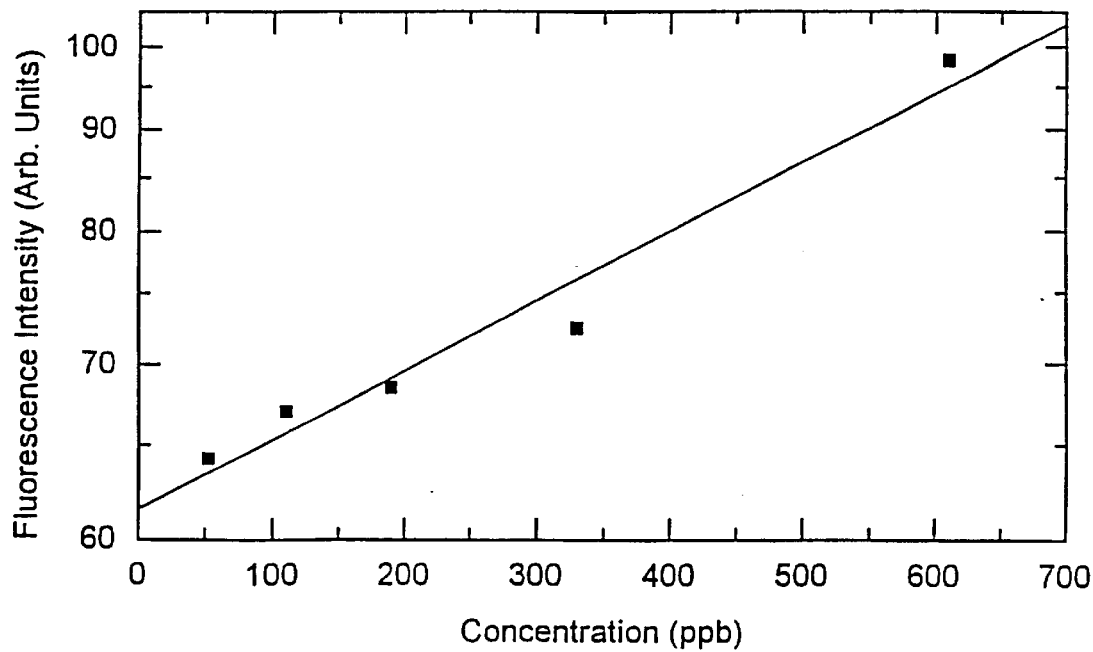
FIG. 6 shows the fluorescence of DiIC$_1$(5) dye in Naifon® polymer upon exposure to DMMP vapor.
Figure 7:
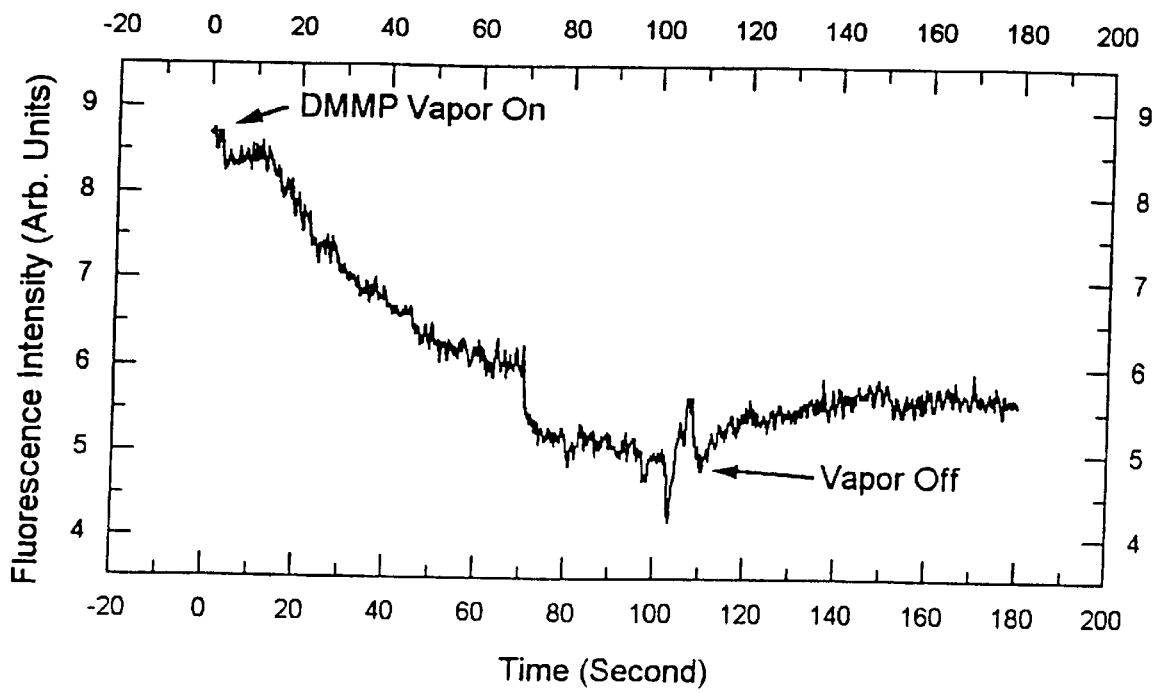
FIG. 7 shows a change of fluorescence when DMMP vapor interacts with nile red doped PVP polymer film.

Oven-dried samples showed considerable fluorescence prior to exposure to DMMP vapor, and showed quenched fluorescence after exposure as shown in FIG. 3. Examination of the UV-Vis spectrum of the oven-dried film showed a sharp absorption peak at 630 nm wavelength prior to exposure to DMMP which shifted to 620 nm after exposure. DiIC$_1$(5) is a cationic dye that can interact with the micelle structure. It may be postulated that when the film is dried at room temperature, some solvent remains in the Nafion® membrane. The dye/solvent interaction within the Nafion® micelles results in a broad absorption spectrum. When the film is baked at 120° C., most of the solvent is evaporated. The dye is forced to migrate into the micelles and displays a sharp absorption peak. It was found that the use of a photomultiplier tube as the detector in the fluorescence measurements provided repeatable detection of DMMP in nitrogen at concentrations below 10 ppm. FIG. 4 shows the change of fluorescence intensity in response to different concentrations of DMMP. The relationship is linear when the y-axis is plotted using a reciprocal scale. In an attempt to determine the detection limit of DMMP using the PMT, concentrations of DMMP between 0.9–13 ppm were used. FIG. 5 shows the change of fluorescence intensity of a DiIC$_1$(5)/Nafion® coated film when exposed to 0.9 to 13 ppm of DMMP. The error bars were obtained using standard deviation of two sets of experiment measurements. FIG. 6 shows the response of the DiIC$_1$(5)Nafion® coated film at lower concentrations of DMMP. The measurable response at 50 ppb represented the lowest detectable concentration of DMMP generation by permeation tube. Oxazine 750 perchlorate was also immobilized in a Nafion® matrix and excited with a diode laser at 675 nm. The fluorescence intensity on a reciprocal scale decreases with increasing DMMP concentration, as shown in FIG. 7.

Figure 8:
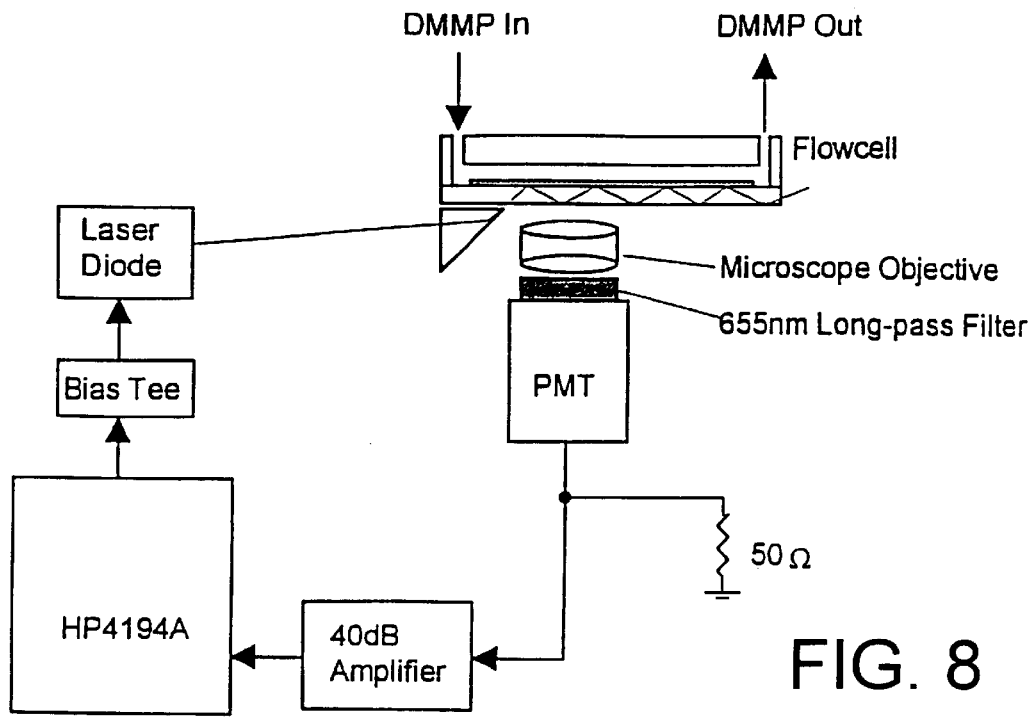
FIG. 8 shows a setup for phase-resolved fluorescence measurement.
Figure 9:
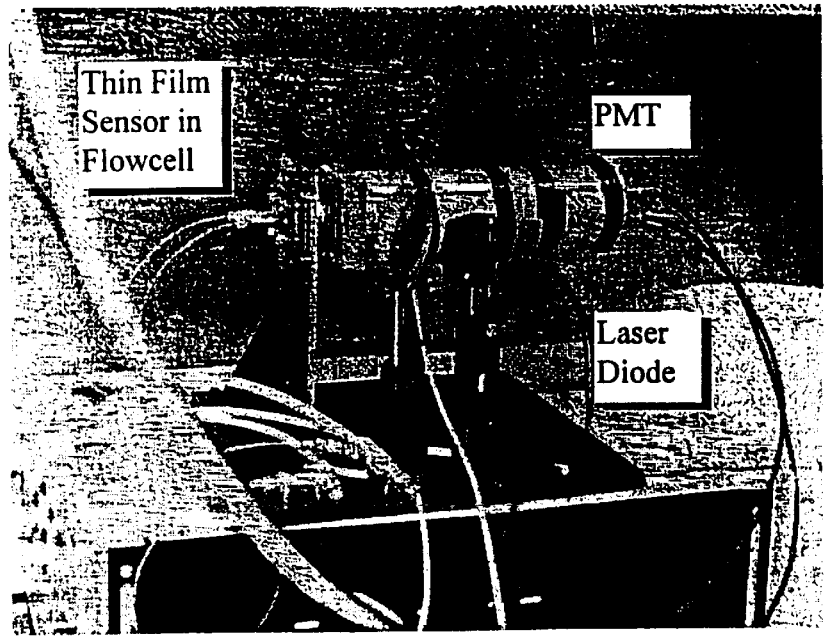
FIG. 9 is a photograph of an optical setup for detection of Sarin Nerve Agent.
Figure 10:
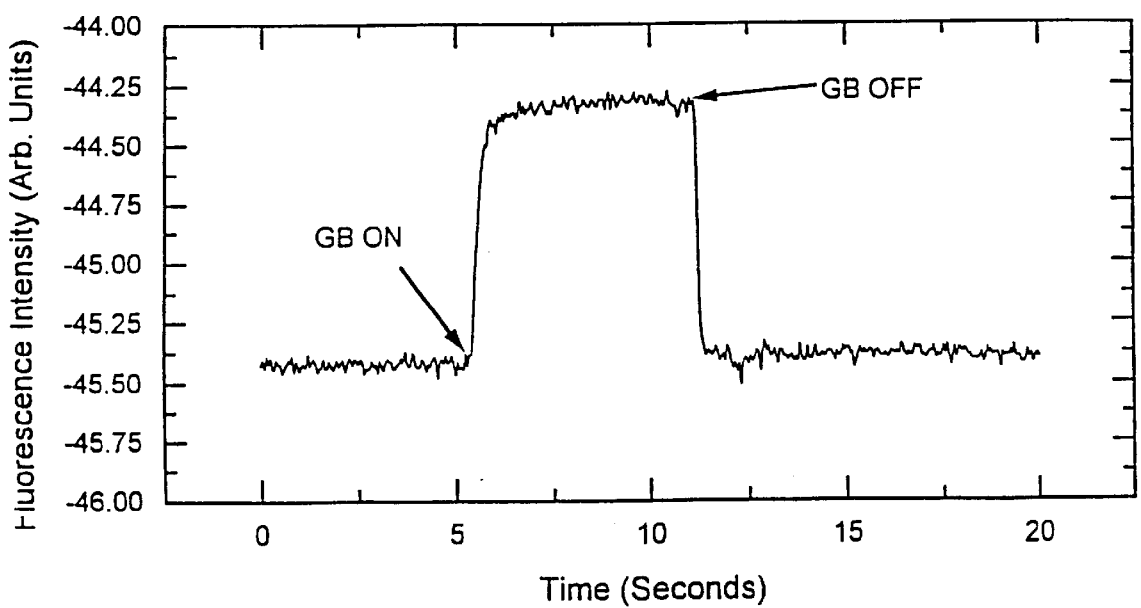
FIG. 10 shows a change of fluorescence intensity when the film is exposed to Sarin at 0.52 mg/m$^3$.
Figure 11:
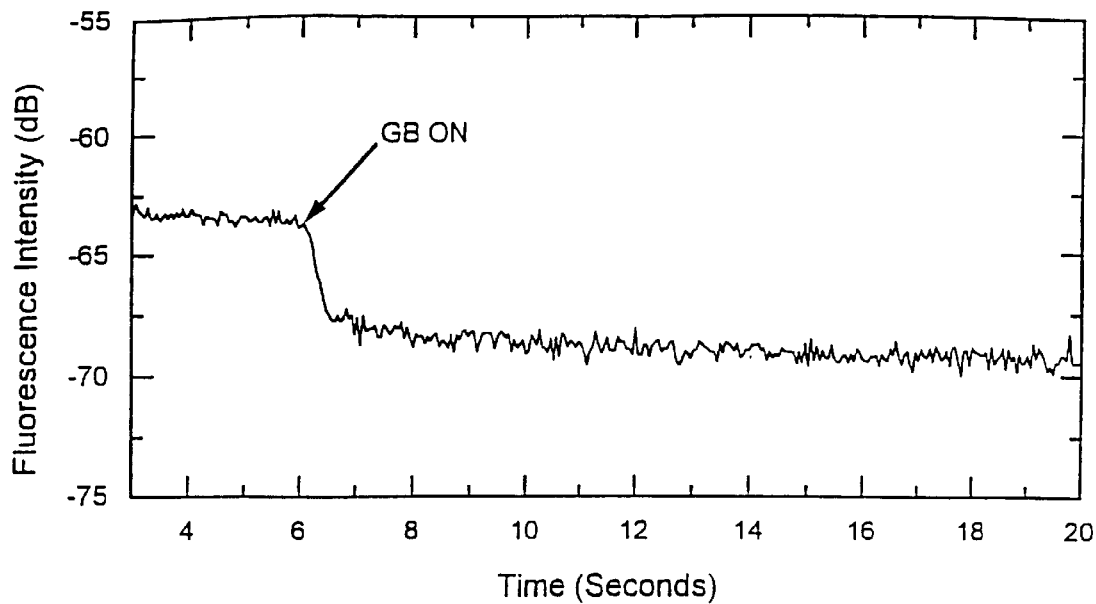
FIG. 11 shows a change of fluorescence intensity when DiIC$_1$(5) in Naifon® film is exposed to 0.0099 mg/m$^3$ concentration of Sarin.
Figure 12:
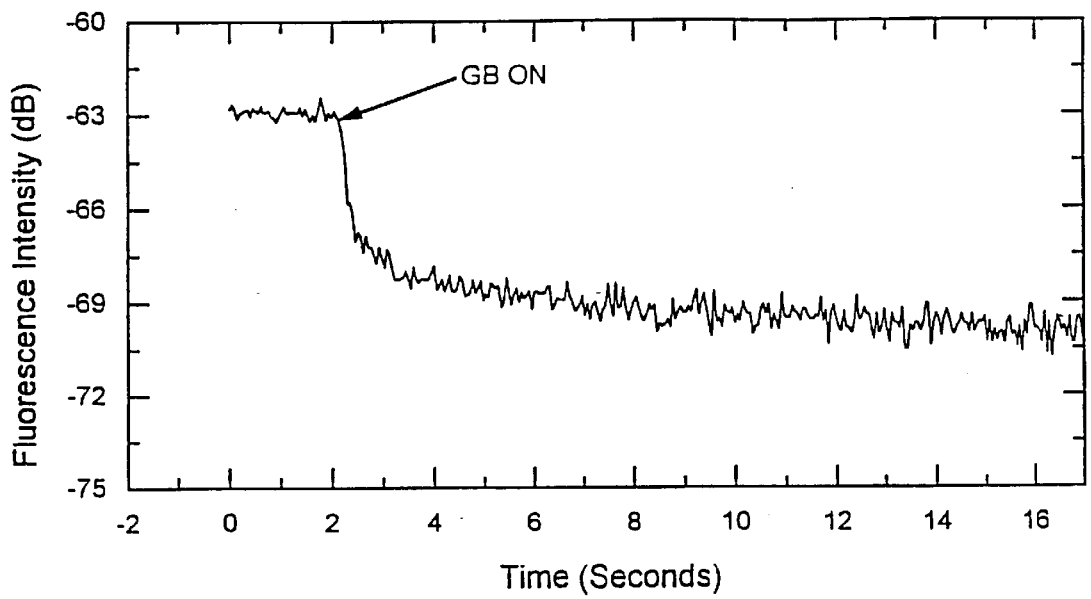
FIG. 12 shows a change of fluorescence intensity when DiIC$_1$(5) in Naifon® film is exposed to 0.029 mg/m$^3$ concentration of Sarin.

$DiIC_1(5)$Nafion® coated film was found to be sensitive to nerve gases. FIG. 8 shows the experimental configuration used for detection of nerve gases. FIG. 9 shows a photograph of the experimental setup for detection of Sarin (GB) using attenuated total reflection methods of fluorescence excitation. This setup employed a semiconductor diode laser at 635 nm as an excitation source. The concentration of Sarin was calibrated through the use of a miniCAMS system operating in a flame-photometric mode. The data from FIG. 10 indicates a response time of less than 1 second and a similar clear-down time. FIG. 11 and FIG. 12 show the response of 1,1',3,3,3',3'-hexamethylindotricarbocyanine iodide ($DiIC_1(5)$) in Nafion® coated onto soda lime glass slide to Sarin (GB) at concentrations of 0.0099 mg/m$^3$ (1.7 ppb) and 0.029 mg/m$^3$ (5 ppb), respectively. It may be noted that the response at these concentrations is not a linear function of concentration. The response was observed to be somewhat reversible. Also noted during testing was the binary response (on or off) of the fluorescent probe to concentrations of GB in excess of 1.7 parts-per-thousand. Reduction of the agent concentration to 500 parts-per-trillion elicited a measurable change in probe fluorescence (data not shown) but continued to provide a near on-off response for presentation of the agent and cleardown. Indications of the existence of a concentration range at which the probe response could be quantitative were found when live agent located a distance from the probe was allowed to diffuse in still air to the probe. The fluorescence amplitude in the presence of that diffusion was slowly increasing, indicating that the sensor may respond quantitatively at concentrations below 500 parts-per-trillion.

As a second example, work was performed to screen polymer-fluorophore combinations for sensitivity to dimethyl methyl phosphonate (DMMP). Screening work involved the acquisition and deposition of poly(ethylene-maleic anhydride) (PEM), poly(vinyl pyridine) (PVP) and poly(4-vinylphenol) bromonated (PVPOH-Br) on glass slides after doping with nile red (Aldrich) or nile blue (Aldrich). PEM was prepared by adding 0.2 g of polymer to 20 ml of acetone. PVP was prepared by dissolving 0.1 g of polymer in 20 ml of chloroform. Probes were prepared using a $3.9 \times 10^{-4}$M solution of nile red or $1.56 \times 10^{-3}$M solution of nile blue added directly to the PEM or PVP material. Solutions containing polymer and dye were deposited on glass slides to a thickness in the range 0.06 to 1.0 mm. Samples of nile red/PEM, PVP or PVPOH-Br were excited using the 488 nm line of a 1 mW argon-ion laser. Samples of nile blue/PEM were excited using a 3 mW helium-neon laser emitting at 632.8 nm or a diode laser emitting at 635 nm. Interaction with vapor DMMP was accomplished either by placing the sample in the vicinity of the liquid at room temperature or by heating the liquid to increase the vapor pressure.

Figure 13:
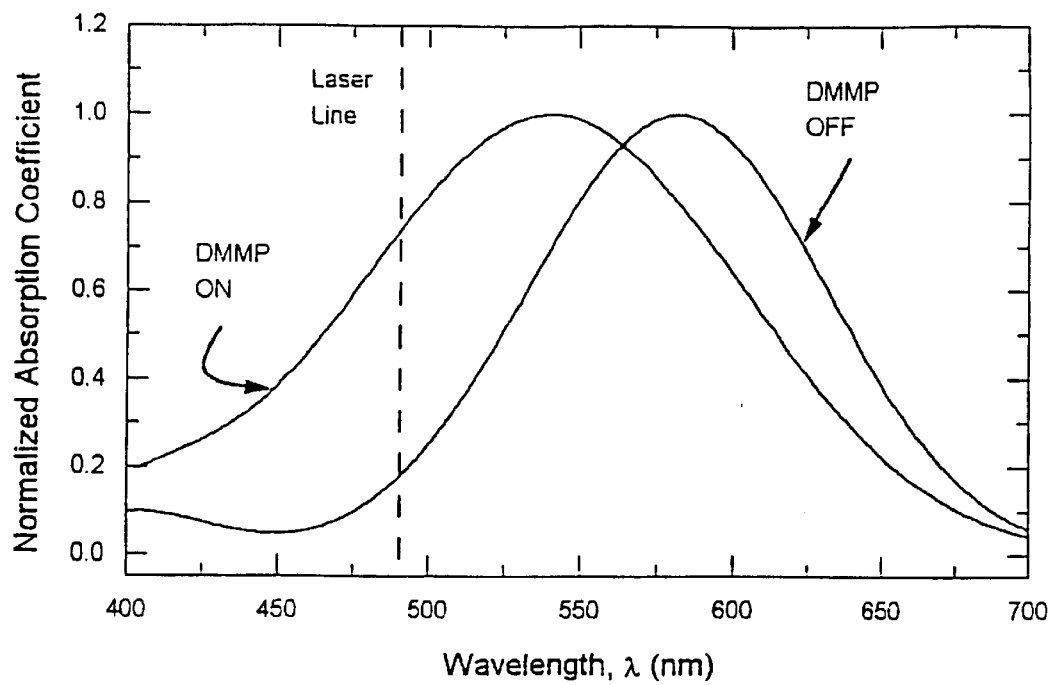
FIG. 13 shows a change of absorption spectrum of nile red/PEM polymer upon reaction with DMMP.
Figure 14:
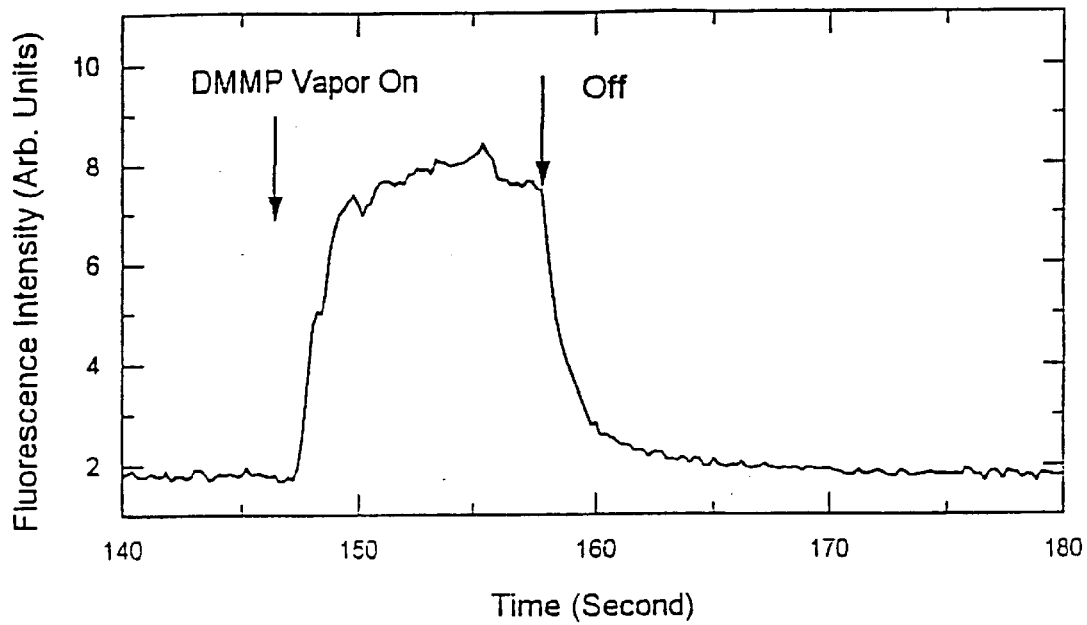
FIG. 14 shows a typical response curve of nile red/PEM film to DMMP vapor.
Figure 15:
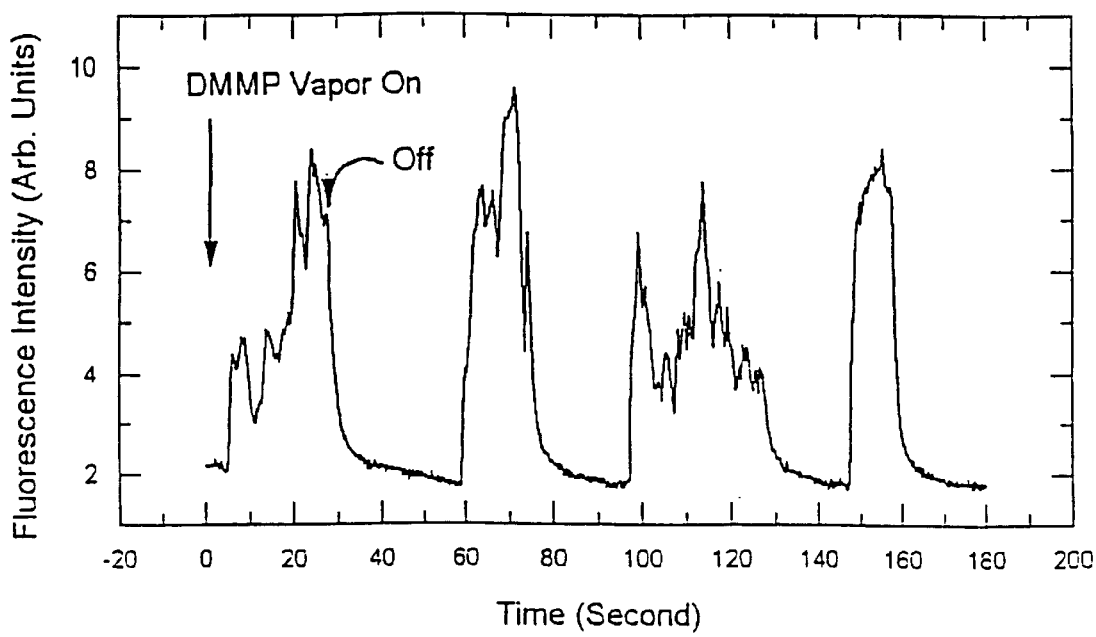
FIG. 15 is a response of the sensor to fluctuations in DMMP vapor concentration.
Figure 16:
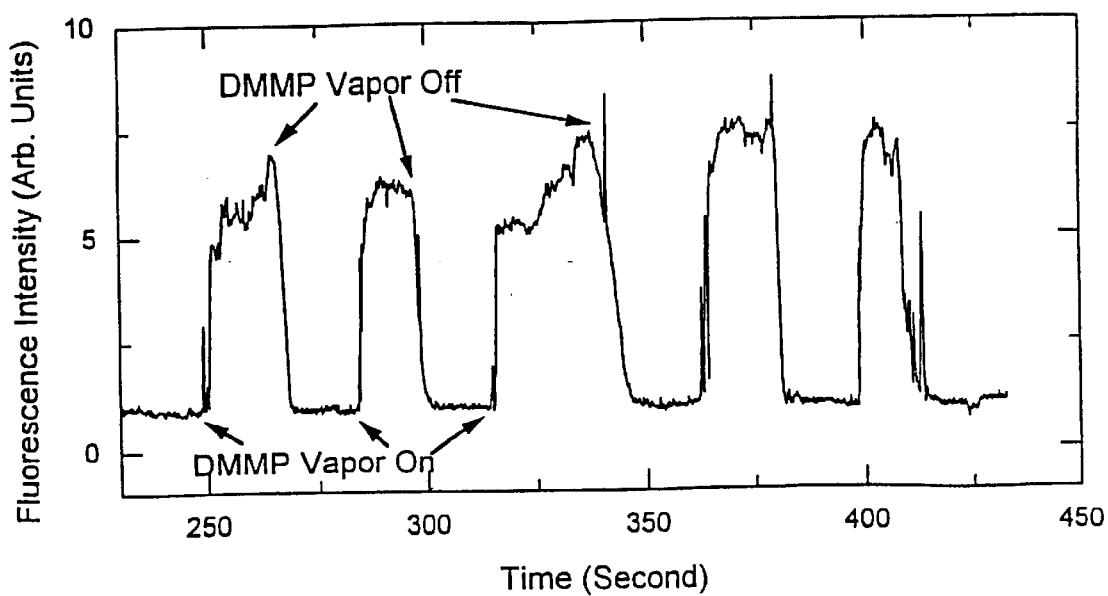
FIG. 16 shows a change of fluorescence when DMMP vapor interacts with nile red doped PVPOH-Br polymer film.
Figure 17:
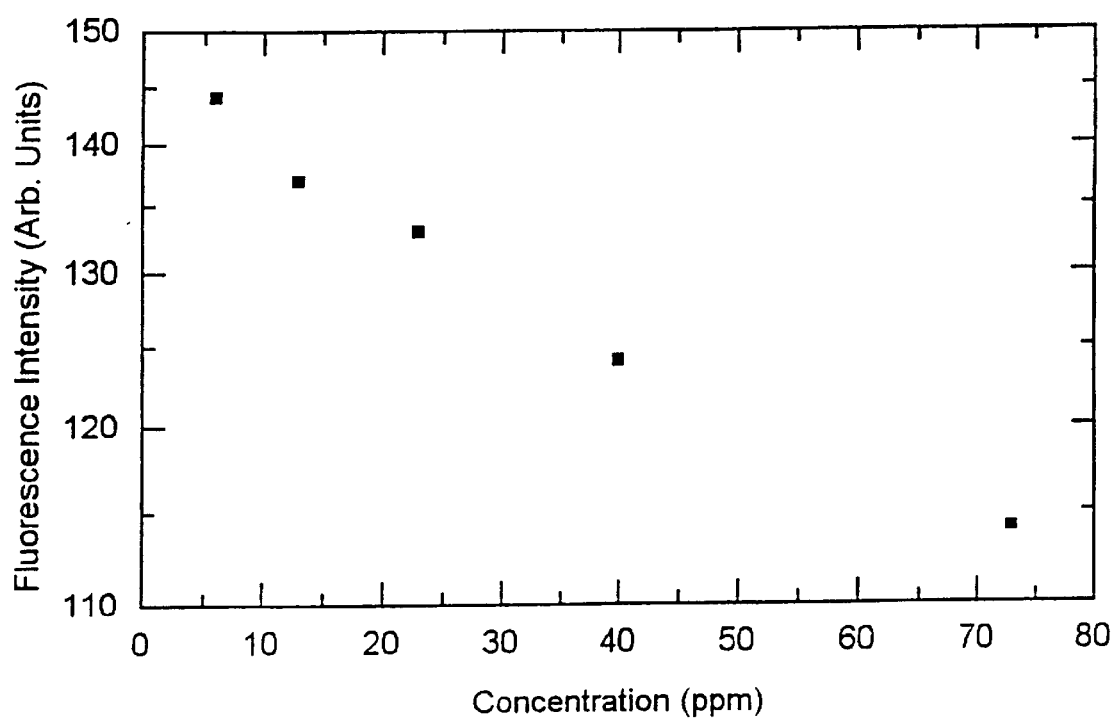
FIG. 17 shows the fluorescence of Oxazine 750 dye in Naifon® polymer upon exposure to DMMP vapor.
Figure 18:
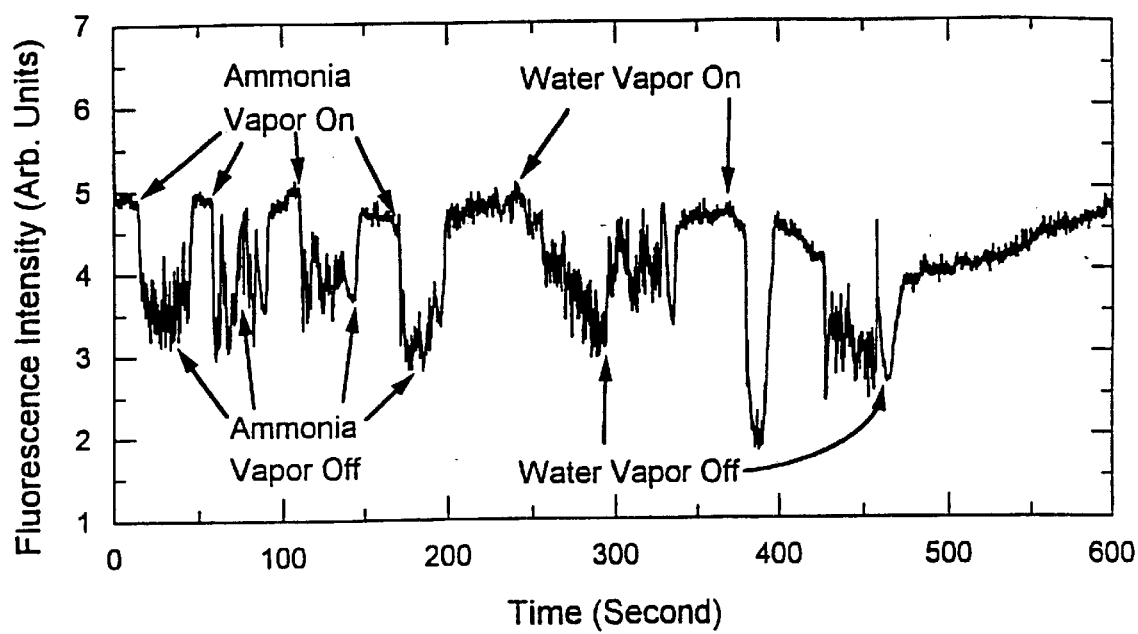
FIG. 18 shows a change of fluorescence when ammonia or water vapor interacted with nile red dope PVP polymer film.
Figure 19:
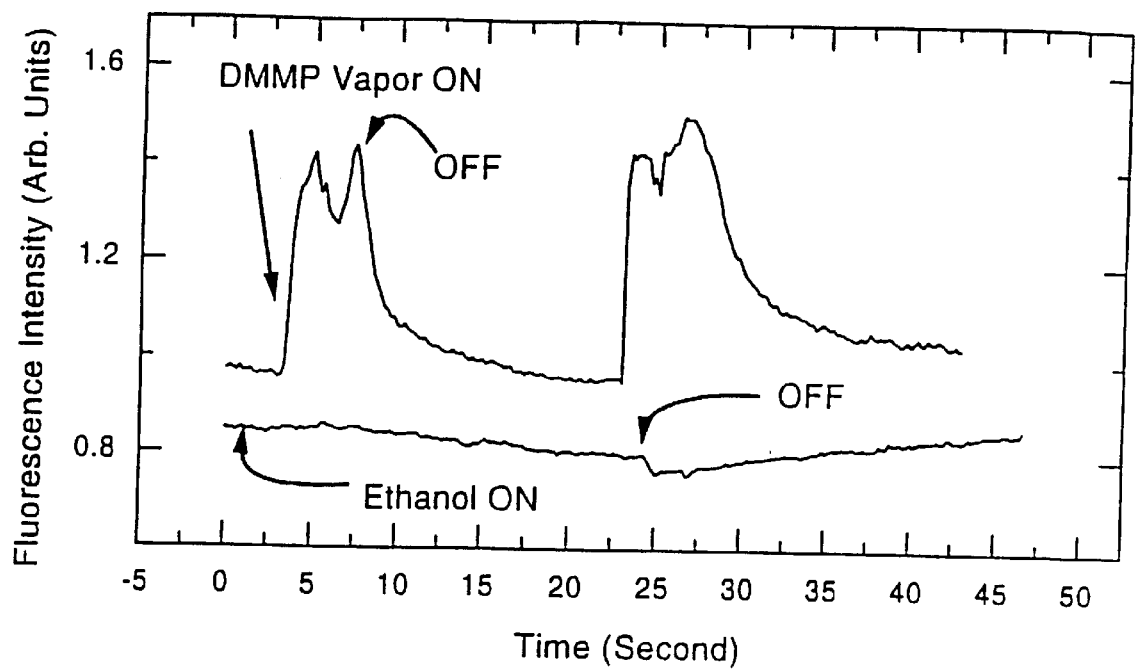
FIG. 19 shows a time response of nile blue/PEM film to DMMP and ethanol vapor.

The absorption spectrum of nile red in PEM was found to change significantly upon exposure to DMMP as shown in FIG. 13. The difference in fluorescence upon excitation at 488 nm and exposure to DMMP may be seen to result directly from the change in absorption at that wavelength. It may be noted that excitation at 450 nm, a wavelength achievable with a blue light emitting diode (LED) equipped with a short wavelength pass filter may provide a similar response in that, in the absence of DMMP, there is virtually no absorption at 450 nm and exposure to DMMP increases the absorption by a factor of 8 or more. FIG. 14 shows the characteristic response of the nile red/PEM probe to vapor DMMP. After exposure to the vapor the sensor fluorescence returns to the pre-exposure value, indicating a degree of sensor reversibility. The figure also demonstrates that the sensor has a very short response time of 2–3 seconds. FIG. 15 shows the variation of sensor response with fluctuations in vapor concentration. The consistent return of sensor fluorescence to pre-exposure values after the vapor pressure of DMMP is reduced provides a reasonable assurance that slight variations in vapor concentration can be monitored. The sensor employing nile red and PVPOH-Br was also tested for its response to DMMP vapor, as shown in FIG. 16. The fluorescence increases with increasing DMMP concentration. The on and off time of the sensor is also on the order of several seconds, compatible with nile red/PEM system. The fluorescence of nile red in PVP was found to exhibit a maximum at approximately 630 nm. On addition of DMMP, the fluorescence maximum was blue-shifted by 5–7 nm and significantly decreased, as shown in FIG. 17. The response of this sensor is in the range of 80–100 seconds. The nile red/PVP film was also exposed to ammonia and water vapor by placing the film in the presence of vapors at room temperature or form the boiling liquid, respectively. The sensor responded reversibly, as shown in FIG. 18. A similar sensor for ammonia has been demonstrated where the reversible response of Oxazine perchlorate immobilized on an etched capillary tube. The response was likely reversible in that the weakly acidic Oxazine dye donates a proton to the weakly basic ammonia. The fluorescence of nile blue in PEM results in an increase in fluorescence. Exposure of the nile blue/PEM film to ethanol results in a decrease in fluorescence, as shown in FIG. 19. The rapid response of nile blue/PEM to DMMP is also shown in FIG. 19.

Further, work was performed to extend the application of this methodology for chemical sensing through incorporating nile blue 690, quinaldine red, phenosafranin, rhodanile blue, Oxazine 170, brilliant crescyl blue, 3,3'-diethylthiatricarbocyanine iodide (DTTC iodide), 1,1'3,3,3',3'-hexamethylindodicarbocyanine iodide (HIDC iodide), IR-144 (Kodak Laboratory Chemicals) and methylene blue in poly(ethylene maleate) or poly(vinyl pyridine). Dye solutions were prepared to $10^{-4}$M using either methanol or acetone as solvent. Poly(vinyl pyridine) coatings were prepared using 3 ml of the dye solution containing methanol solvent and 0.07 g of polymer. Poly(ethylene maleate) coatings were prepared using 3 ml dye solution containing acetone solvent and 0.1 gram polymer. The excitation and emission spectra were obtained using a SPEX fluorimeter with a xenon lamp source. Vapor DMMP was generated by placing approximately 0.0158 g, or 0.0122 mL of liquid DMMP in a heating mantle inside the sample cell and applying current to the heating mantle, resulting in complete vaporization of the drop in 3 to 5 minutes. It is estimated that the polymer/dye probe is exposed to approximately 5 micrograms of material in a 392 cubic centimeter volume. Fluorescence quenching of the polymer/dye probe is measured by comparison of the probe emission in the presence of the vapor to the emission of the probe away from the DMMP vapor. The results of work performed appear in FIGS. 24 and 25. DTTC iodide responds primarily to DMMP and very slightly to temperature or air flow. The quenching of DTTC iodide in Nafion® can be reversed by exposure to concentrated hydrochloric acid vapor. Oxazine 170, Oxazine 750, nile blue A and 1,1',3,3,3',3'-hexamethylindodicarbocuyanine iodide are also sensitive to DMMP when immobilized in Nafion®.

The probes described above were found to be more or less sensitive to ammonia, xylene and ethanol. Experiments were performed to evaluate the use of fluorophores embedded in Nafion® for sensing dissolved ammonia. It was found that solution casting the fluorophore immobilized in Nafion® onto glass slides resulted in films with relatively poor mechanical stability upon immersion in water. The mechanical stability of the films was found to increase after baking in an oxygen atmosphere at temperatures ranging from 100–200° C. Films baked in an oxygen atmosphere are somewhat yellowed and brittle. Baking the films in a nitrogen atmosphere circumvents the yellowing and brittleness problems. Adding around 10% by volume ammonium hydroxide to the solution prior to deposition provides a film whose fluorescence does not degrade with time. When Nafion® coatings are exposed to sodium hydroxide or ammonium hydroxide, the polymer's acidic sulfonate side groups are converted to ionic salts. The counter ion of the salt can then be exchanged with another positively-charged species such as a cationic dye. The ion-exchange properties of Nafion® coatings provide an opportunity of immobilizing chemically-sensitive dyes in the Nafion® matrix. When fluorescent dyes are thus added by ion-exchange, the fluorescence is not as rapidly degraded as when the dyes are codeposited without the addition of a strong base. Ion-exchanged Nafion® films can be completely immersed in water without any harmful mechanical degradation over periods of time in excess of several weeks. Fluorophores immobilized in Nafion® films can be deposited by spin coating or solution casting. The Nafion® polymer is prepared at a concentration of 5% polymer in ethanol, having ammonium hydroxide added. Spin coating in excess of 2000 rpm produces a fairly uniform film estimated to be less than 1 micron thick. After deposition, the sample is baked in a nitrogen oven at 160–190° C. for 2 hours (including a time for ramp-up from room temperature at 5° per minute). The film provides a sensitive probe depending on the fluorophore embedded.

The present invention is responsive to live agents. Probes fabricated from nile blue perchlorate, DiIC$_1$(5) and Oxazine 750 in a Nafion® matrix were exposed to Soman, O-ethyl S-2-diisopropyl aminoethyl methyl phosophono thiolate (VX) and HD in a closed petri dish and different changes in coloration were observed for each of the probes. The findings indicate that Nafion®-based films are responsive to each of those agent materials.

Figure 20:
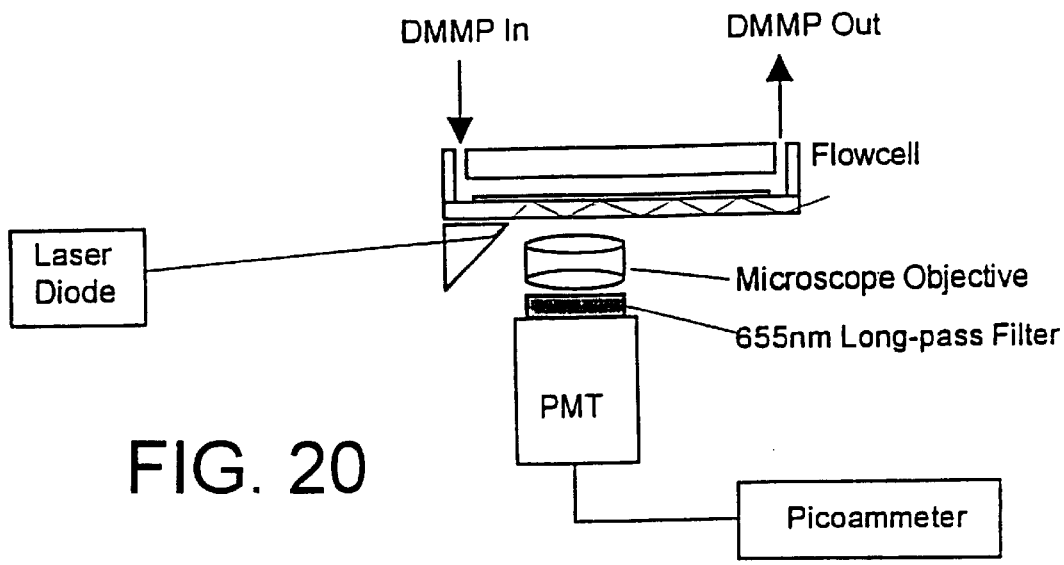
FIG. 20 is a setup for detection of DMMP using a photomultiplier tube.

FIG. 20 shows an embodiment of the sensor having the polymer/dye probe. In one embodiment, a laser diode emitting at 638 nm is the light source and a DiIC$_1$(5)/Nafion® is subjected to evanescent wave excitation. Fluorescence is collected is collected using a 5x microscopic objective and a photomultiplier tube equipped with a 665 nm long-pass filter. The output current is measured using a picoammeter. A lithographically fabricated laser sensor having a fluorophore/polymer probe within the laser cavity can be created for reducing problems associated with coupling the laser light to a single mode optical fiber and integrated optical sensor.

To employ chemometric pattern recognition procedures for on-line detectors, it is necessary to have a series of films that respond reversibly to the analyte of interest as well as interferents expected during field operation. The present invention provides sensors based on PEM and PVP polymers that respond reversibly and differentially to analytes, such as DMMP, and interferents such as ammonia or ethanol. Nafion® has an unparalleled response to nerve agents and DMMP. Films of nile blue A immobilized in Nafion® were exposed to xylene and ammonia vapor. With diode laser excitation at 638 nm, the films showed a marked increase in fluorescence upon exposure to 50 ppm xylene or 2 ppm ammonia vapor. When 1,1',3,3,3',3'-hexamethylindodicarbocuyanine iodide in Nafion® is exposed to those interferents, there was a sharp decrease in fluorescence in the presence of xylene and a sharp increase in fluorescence in the presence of ammonia. The responses to both probes were relatively irreversible to the interferents selected. That is in sharp contrast to the response of either probe to DMMP or live agent where the response is reversible. It was found that the absorption changes associated with exposure to ammonia at the parts per hundred range could be reversed upon heating for an hour or more. More rapid reversal was found in probes exposed to lesser concentrations of interferant.

Figure 21:
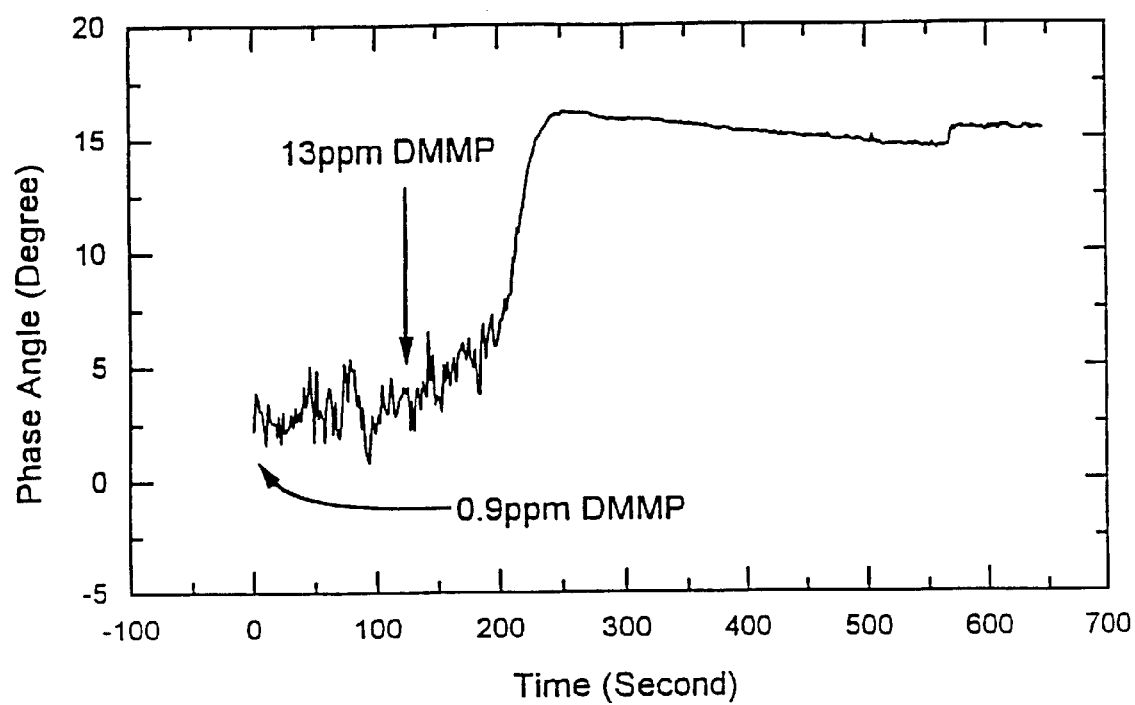
FIG. 21 shows a change in phase angle of fluorescence of DiIC$_1$(5)/Naifon® film upon exposure to DMMP vapor at 10 Mhz modulation frequency.
Figure 22:
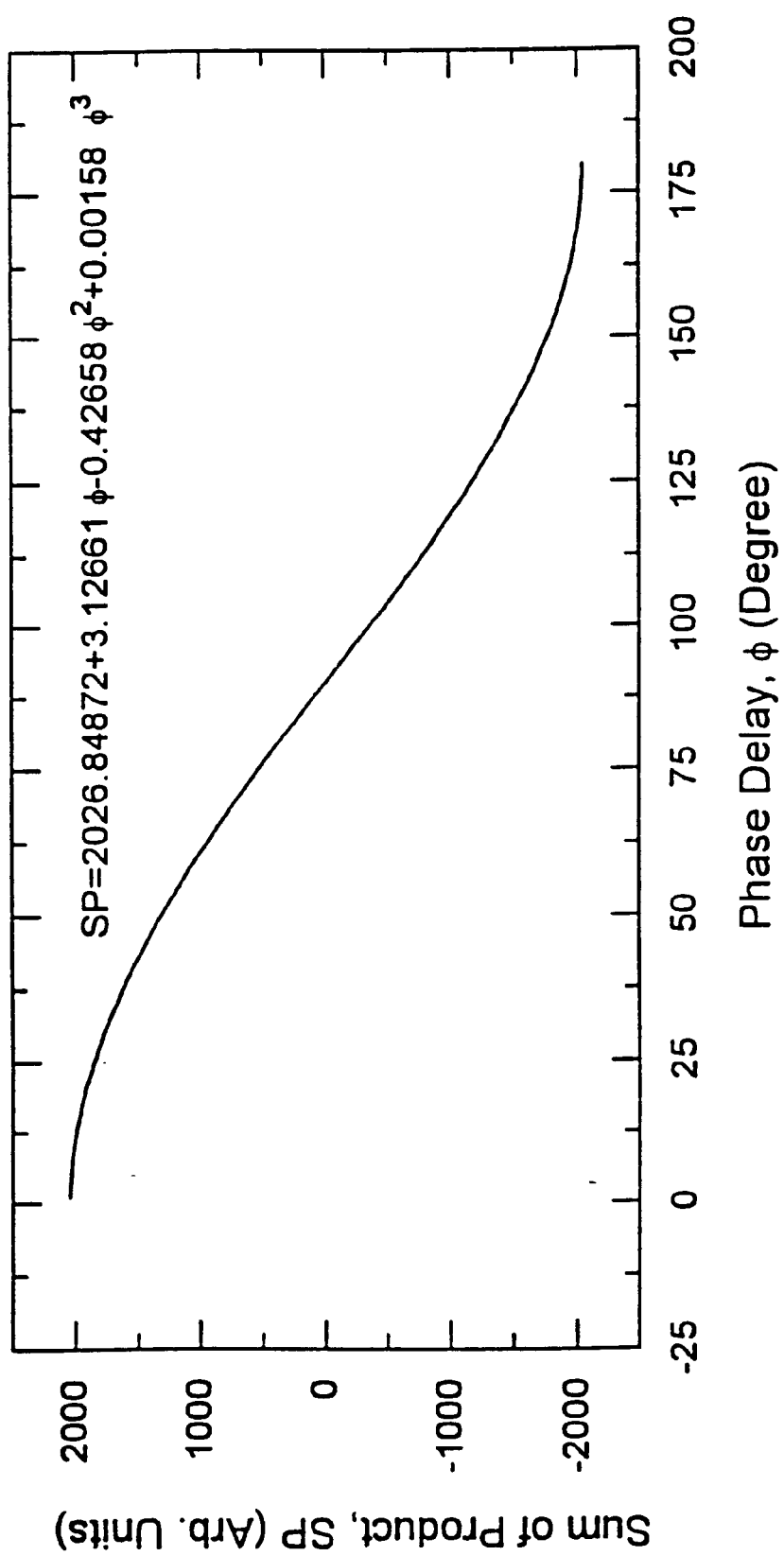
FIG. 22 is a simulation of change of sum of product to phase angles.
Figure 23:
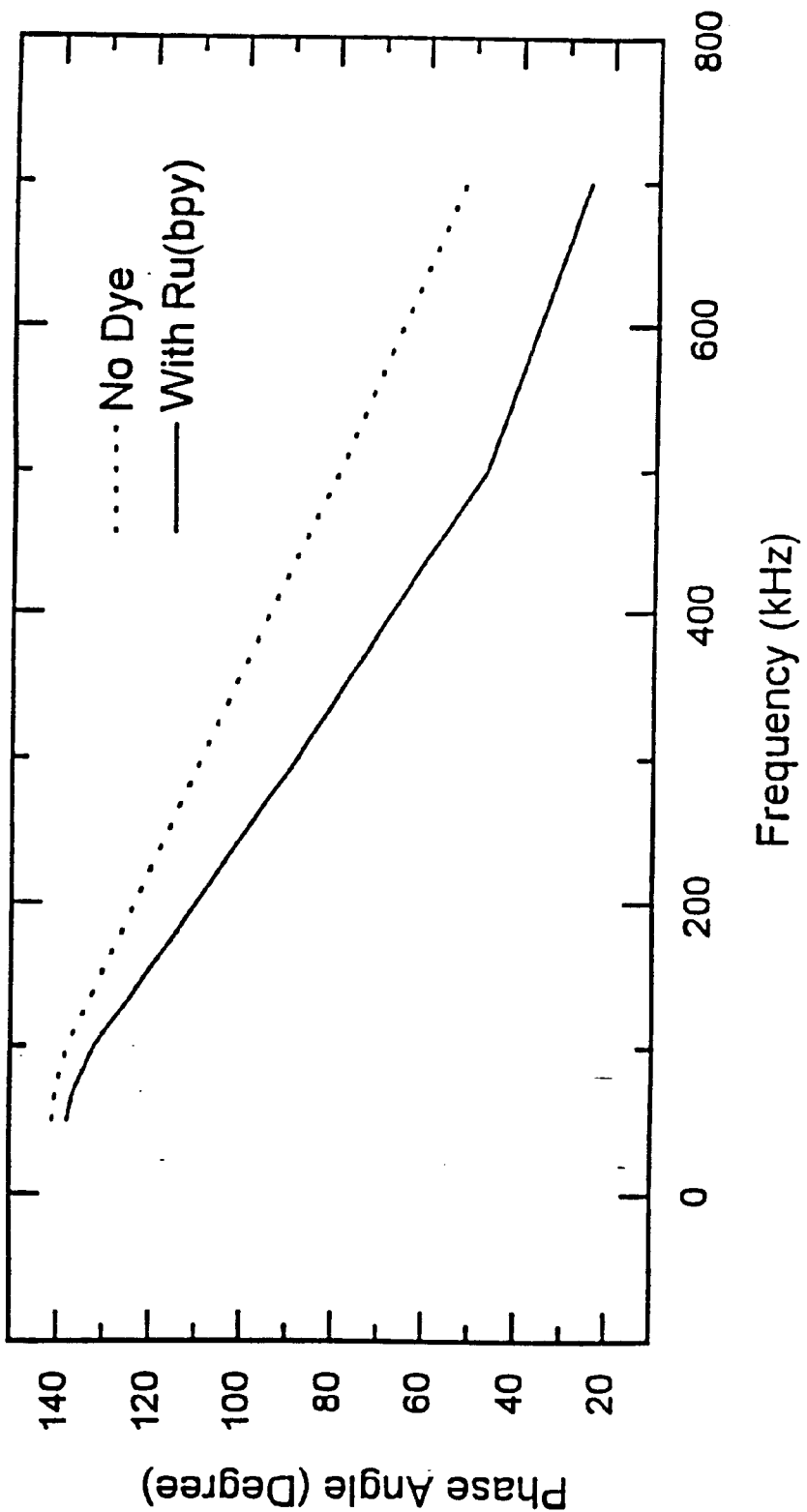
FIG. 23 is a phase delay of no dye(reference phase) and Ru(bpy) in water.

The present invention also encompasses a fluorescence decay instrument using a gain-phase analyzer. A schematic of the system is shown in FIG. 8. Direct modulation of the laser diode at up to 100 MHz is provided by a gain-phase analyzer (HP4194A) which is also used to measure phase angle. The laser diode is biased by injection current to produce an output power through the use of a bias tee. Experiments were performed to detect the change of fluorescence decay when a DiIC$_1$(5)/Nafion® probe was exposed to 0.9–13 ppm of DMMP. FIG. 21 shows a phase angle difference of approximately 13 degrees between 0.9 ppm and 13 ppm of DMMP. Work to assemble a fluorescence decay instrument based on commercially available mixers, low-cost digital signal generators and digital signal processing resulted in an instrument capable of detecting fluorescence lifetime of ruthenium metal-ligand fluorophores. The instrument operates by calculating the sum of the products and at discrete samples of the signal and reference waveforms. The actual phase difference is found by normalizing the signal and reference waveforms and comparison to a fitted equation shown in FIG. 22. Data obtained using this instrument in monitoring the fluorescence of Ruthenium trisbipyridal is shown in FIG. 23. The data was acquired using a light emitting diode emitting at 450 nm and an amplified photodetector as the detector. The incorporation of light emitting diode excitation and amplified photodiode detection in fluorescence decay instruments represents an advance over state-of-the-art instruments.

Light emitting diode (LED) based sensors provide advantages in system cost and reliability. An optical waveguide based on a silicon substrate coated with 3 to 5 mm of silica, 1.5 mm of silica doped with titania or phosphate pentoxide (to provide a refractive index difference of 0.01 from the silica layer below), a 2.5 mm silica buffer layer, 35 nm of silver and a 80 nm silica tuning layer. The structure provides a field enhancement for fluorescence excitation of 1800 with an associated loss of TM mode field of 40 dB/cm. Altering the buffer layer thickness to 2 mm increases the evanescent field intensity to 2400 but increased the TM losses to 170 dB/cm. The use of a semiconductor diode laser either to excite an optical waveguide configured in this manner or in a configuration where the semiconductor diode laser waveguide is extended beyond the end facets provides a compact optical chemical sensor with reduced dimensions and increased sensitivity.

While the invention has been described with reference to specific embodiments, modifications and variations of the invention may be constructed without departing from the scope of the invention, which is defined in the following claims.

We claim:

1. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye is a fluorescent dye, and wherein the polymer matrix is selected from the group consisting of a poly(ethylene-maleic anhydride) matrix, a poly(vinyl pyridine) matrix, a poly(4-vinyl-phenol) bromonated matrix, and a perfluorosulfonic acid/polytetrafluoroethylene copolymer matrix.

2. The apparatus of claim 1, wherein the analyte of interest is selected from the group consisting of dimethyl methylphosphonate, Sarin, benzene, xylene, toluene and ammonia.

3. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye is a membrane potential sensitive dye and wherein the polymer matrix is selected from the group consisting of a micelle forming polymer matrix and a reverse micelle forming polymer matrix.

4. The apparatus of claim 3, wherein the membrane potential sensitive dye is 1,1'3,3,3',3'-hexamethylindotricarbocyanine iodide, and wherein the matrix is a perfluorosulfonic acid/polytetrafluoroethylene copolymer matrix.

5. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye is a fluorophore dye, wherein the polymer matrix is selected from the group consisting of poly(isoprene/fluoro alcohol) and poly(ethyleneimine), and wherein the analyte of interest is a hydrogen-bond forming material.

6. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye further comprises near-infrared fluorophores.

7. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye is selected from the group consisting of nile red and nile blue, and wherein the polymer matrix is selected from the group consisting of a poly(ethylene-maleic anhydride) matrix and a poly(vinyl pyridine) matrix.

8. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the dye is selected from the group consisting of 5-amino-9-(diethylamino)-benzo[a]phenoxazin-7-ium perchlorate, quinaldine red, phenosafranin, rhodanile blue, 2,3,6,7-tetrahydro-5-(ethylimino)-1H,5H-benzo[a]phenoxazin-[8,9,10-ij]quinolizin perchlorate, 5,9-bis(ethylamino)-10-methyl-benzo[a]phenoxazin-7-ium perchlorate, brilliant cresyl blue, 3,3'-diethylthiatricarbocyanine iodide, 1,1'3,3,3',3'-hexamethylindodicarbocyanine iodide, CAS-Reg. 54849-69-3 and methylene blue and wherein the polymer matrix is selected from the group consisting of a perfluorosulfonic acid/polytetrafluoroethylene copolymer matrix, a poly(ethylene maleate) matrix and a poly(vinyl pyridine) matrix.

9. A fluorescent probe apparatus for use in a sensor, comprising a polymer matrix and a dye immobilized in the matrix, wherein the polymer matrix has an affinity for an analyte of interest and wherein the dye has little or no sensitivity to the analyte of interest when excited by an excitation source in a free state but has significant sensitivity to the analyte of interest when excited by the excitation source when immobilized in the matrix, wherein the polymer matrix has dimensions that change when introduced to the analyte of interest, wherein the dye is a membrane potential fluorescent dye whose fluorescence is determined by a degree of aggregation of the dye with the polymer.

10. The apparatus of claim 9, wherein the dye is 1,1'3,3,3',3'-hexamethylindodicarbocyanine iodide.

* * * * *